US 6,689,146 B1

(12) United States Patent
Himes

(10) Patent No.: US 6,689,146 B1
(45) Date of Patent: Feb. 10, 2004

(54) POWERED SURGICAL HANDPIECE WITH INTEGRATED IRRIGATOR AND SUCTION APPLICATION

(75) Inventor: David M. Himes, Los Gatos, CA (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 09/302,148

(22) Filed: Apr. 29, 1999

(51) Int. Cl.[7] .................................................. A61B 17/32
(52) U.S. Cl. ........................................ 606/167; 604/22
(58) Field of Search ................................ 606/167, 168, 606/169, 170–180, 79, 80, 86, 96; 604/22, 32, 33, 34, 35, 66, 67, 247, 248, 249

(56) References Cited

U.S. PATENT DOCUMENTS

| 4,705,038 A | | 11/1987 | Sjostrom et al. | |
| 4,747,820 A | * | 5/1988 | Hornlein et al. | ............... 604/22 |
| 5,203,769 A | * | 4/1993 | Clement et al. | ............... 604/32 |
| 5,269,794 A | | 12/1993 | Rexroth | |
| 5,492,527 A | | 2/1996 | Glowa et al. | |
| 5,669,876 A | * | 9/1997 | Schechter et al. | ............ 604/50 |
| 5,685,838 A | | 11/1997 | Peters et al. | |
| 5,916,231 A | | 6/1999 | Bays | |
| 6,007,556 A | * | 12/1999 | Kablik et al. | ................ 606/180 |
| 6,010,477 A | | 1/2000 | Bays | |
| 6,042,593 A | | 3/2000 | Storz et al. | |
| 6,152,941 A | | 11/2000 | Himes et al. | |

OTHER PUBLICATIONS

Arthrotek Shaver, photographs (8 photographs—4 sheets) Mar., 1999.
Epstein, Pub. No. US 2001/11162 A1, Aug. 2, 2001.*

* cited by examiner

*Primary Examiner*—Lee Young
*Assistant Examiner*—Lien Ngo
(74) *Attorney, Agent, or Firm*—Flynn, Thiel, Boutell & Tanis, P.C.

(57) ABSTRACT

A powered surgical handpiece (20) and a complementary cutting accessory (22). The accessory includes a rotating hub (63) in which magnets (124) are seated. An inner tube (79) with a cutting head extends from the rotating hub. A static hub is (46) located over the rotating hub. An outer tube (60) extends from the static hub over the inner tube. The static hub is formed with a inlet bore (54) through which irrigation fluid is introduced into the annular gap between the two tubes. The rotating and static hubs seat in the body of the handpiece. The handpiece has a coupling assembly (32) that engages the static hub to hold the cutting accessory in place. There is a stator (122) in the handpiece that surrounds the rotating hub. Collectively, the stator and the magnets in the rotating hub define a motor (26) that rotates the rotating hub and the inner tube. An irrigation line (36) supplies irrigating fluid to the handpiece. The irrigation line is connected to an inlet fitting (108) that is part of the coupling assembly. When the coupling assembly is set to engage the static hub, the inlet fitting is automatically coupled to the inlet bore to serve as conduit for introducing irrigation fluid into the cutting accessory. A suction may be drawn from the handpiece through the inner tube. A manually set valve member (42) regulates whether the inner tube is placed in communication with the conduit through which the suction is drawn or the irrigation line.

56 Claims, 13 Drawing Sheets

POWERED SURGICAL HANDPIECE WITH INTEGRATED IRRIGATOR AND SUCTION APPLICATION

FIELD OF THE INVENTION

This application relates generally to powered surgical handpieces such as those employed in endoscopic surgery. More particularly, this invention is directed to a powered surgical handpiece that includes an irrigator for applying fluid to a surgical site, a suction conduit for drawing fluid from the site, a means for clearing the suction conduit and a motor for actuating a complementary cutting accessory.

BACKGROUND OF THE INVENTION

The powered handpiece has evolved into an important tool for performing surgical procedures. A typical powered handpiece includes a housing that contains an electrically driven motor. A coupling assembly is attached to one end of the handpiece. The coupling assembly is used to releasably secure a cutting accessory to the motor so that the motor, when energized, actuates the cutting attachment. The development of powered surgical handpieces and their complementary cutting accessories has made it possible to cut, shape and remove both hard and soft body tissue at faster rates and with a higher degree of accuracy than was possible with the manually powered tools that preceded them.

When a cutting attachment is actuated, the cutting action causes loose tissue and other debris to develop at the surgical site. This material is removed by applying an irrigation fluid to the site and also drawing a suction from the site. The irrigation fluid serves as a transport media for carrying the debris; the suction draws away the fluid and the entrained debris. In order to perform this irrigation and suction, some cutting attachments are provided with conduits through which fluid is applied to and drawn from the surgical site. For example, cutting attachments designed to perform endoscopic surgery or sinus surgery often include a static outer sleeve in which a rotating tube is fitted. The head of the rotating tube is provided with some type of cutting surface or cutting member. Each of these attachments is further shaped so that irrigation fluid can flow to the surgical site through the annular channel between the rotating tube and the static sleeve. The inner rotating tube is further provided with an opening adjacent the head through which a suction is drawn from the surgical site. Thus, the inner tube serves as the conduit through which the irrigation fluid and debris are removed from the surgical site.

A powered handpiece intended for use with the above cutting attachments is designed with complementary features that facilitate the drawing of the suction away from the surgical site. Specifically, this type of handpiece is provided with a suction bore to which a suction pump is applied. The coupling assembly allows fluid flow from the inside of the rotating tube to the suction bore. Moreover, the handpiece is provided with a valve for regulating fluid flow through the suction valve. Thus, a surgeon using this type of handpiece can, with one hand, both manipulate the cutting accessory and regulate the rate at which fluid is drawn from the surgical site.

While current handpieces have provided useful for both driving cutting attachments and drawing a suction, there are some disadvantages associated with their use. In particular, current handpieces and their complementary cutting attachments are designed so that irrigation fluid is introduced into the annular channel through a supply line that is separate from the handpiece. While this supply line may be attached to a handpiece, it has a free end that is typically located forward of the handpiece coupling assembly. The free end of this line has to be manually fitted to an inlet luer integral with the static sleeve. When, during a surgical procedure, the doctor wants to switch cutting attachments, this line must first be removed from the cutting attachment being separated from the handpiece. Then, after the new cutting attachment is installed, the supply line must be manually fitted to the new attachment. The time it takes to perform these steps adds to the overall time it takes to perform the surgical procedure.

Moreover, in these surgical handpieces, the motor is in close physical proximity to the path through which the suction fluid flows through the handpiece. Accordingly, these handpieces must be constructed to include sufficient seals that prevent liquid flow into the components forming the motor. However, over time, and owing to the presence of the moving parts against which these seals press, these seals can wear out. Consequently, it is not uncommon for fluid to enter the motor and cause the components forming the motor to corrode and/or malfunction. Once the integrity of these seals diminishes, this corrosion and motor component wear can occur at a relatively fast rate because the fluid drawn through the handpiece suction is saline.

Also, occasionally, debris can clog the cutting accessory rotating tube through which the suction is drawn from the surgical site. This clogging is especially prone to occur in cutting accessories designed for performing sinus surgery. This is because the diameter of the bore through which this suction flow travels is relatively narrow. Presently, there are two ways a surgeon can try to remove this type of clog in order to reestablish suction at the surgical site. One method involves introducing a large quantity of irrigation fluid into the surgical site. The surgeon takes this action by momentarily running the irrigation pump used to supply fluid at a high speed/high flow flush setting. The introduction of this large quantity of water causes a large fluid pressure head to develop in the rotating tube upstream of the clog. If the conditions are right, the pressure head of this fluid forces the clog-causing debris to flow downstream out of the rotating tube. One problem with this clog removal technique is that the switches for regulating the irrigation pump are typically located off the handpiece. In order for the surgeon to be able to control the pump, he/she must actuate a separate foot or hand switch or instruct an assistant to perform this operation. In each of these situations, the surgeon may have to significantly divert his/her attention from the actual surgical procedure being performed. Still another problem with this method of clog removal is that, often, it simply does not work. Then, the surgeon is left with a situation in which excess fluid has been introduced into the patient.

The second method of clog removal is more mechanical. This method involves running a rigid wire down the rotating tube in order to force the clog out of the tube. When a surgeon has to take this action, he/she must first withdraw the cutting attachment from the surgical site. Then, once the clog is removed, the cutting attachment must be repositioned so that the surgical procedure can be completed. The need to perform these tasks adds to the overall time it takes to perform the surgical procedure.

SUMMARY OF THE INVENTION

This invention relates to an improved powered surgical handpiece and a cutting accessory for use with the handpiece. This invention includes a motor that has a rotor integral with the cutting accessory and complementary windings that are integral with the handpiece. The handpiece has a coupling assembly for holding the cutting attachment to the handpiece that has a conduit through which irrigation fluid is introduced into the attachment for application to the surgical site. The handpiece of this invention also has a valve for regulating fluid flow through the conduit through which a suction is normally drawn. Depending on the setting of this valve, a suction can be drawn through the cutting attachment, the suction shut off or irrigation fluid can be introduced into the suction conduit in order to flush out any debris lodged in the conduit.

BRIEF DESCRIPTION OF THE DRAWINGS

The invention is pointed out with particularity in the claims. The above and further features of this invention may be better understood by reference to the following description taken in conjunction with the accompanying drawings in which:

DETAILED DESCRIPTION

Figure 1:
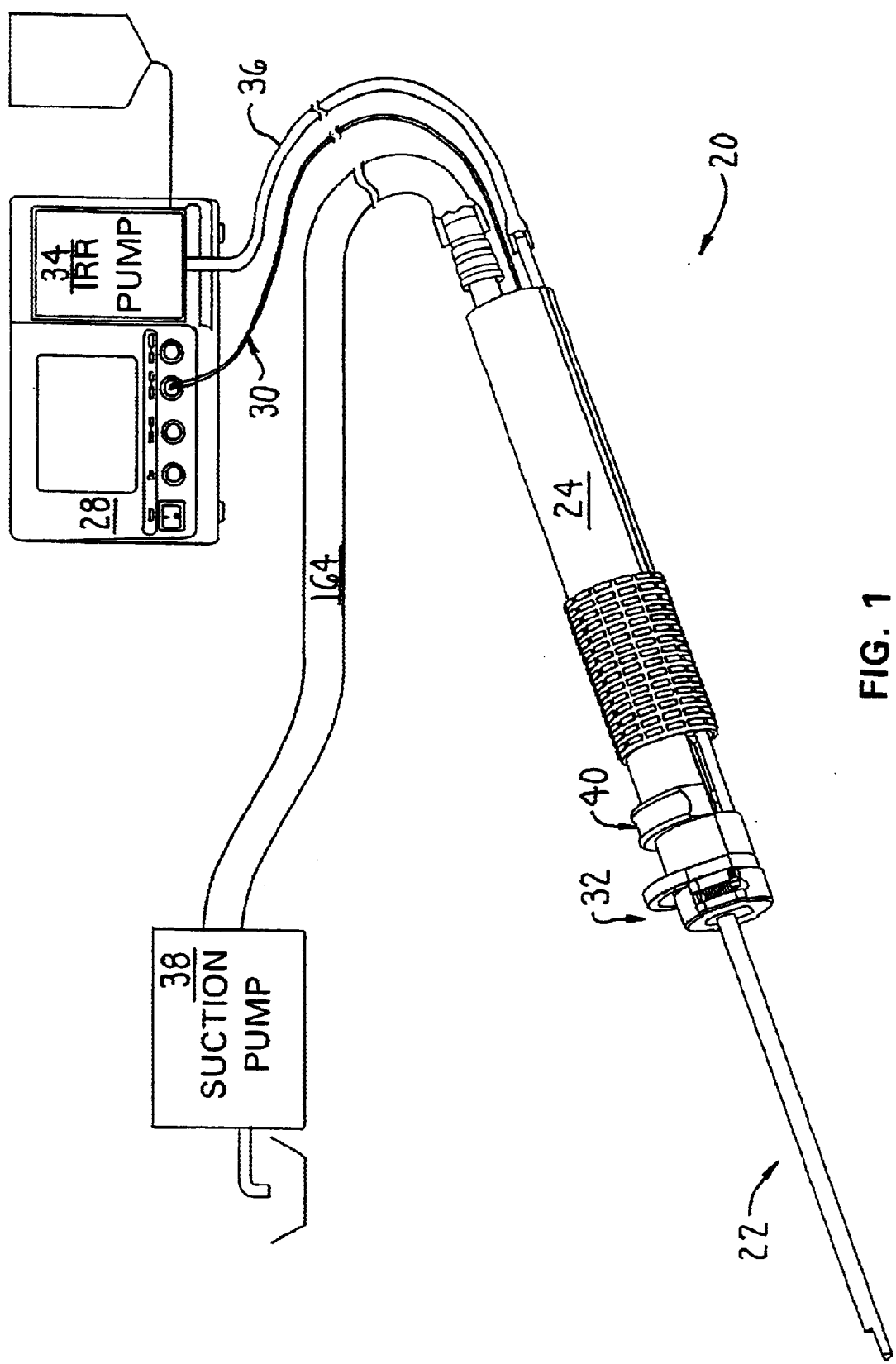
FIG. 1 is a perspective view of a powered surgical handpiece of this invention and a complementary cutting accessory attached to the handpiece.
Figure 2:
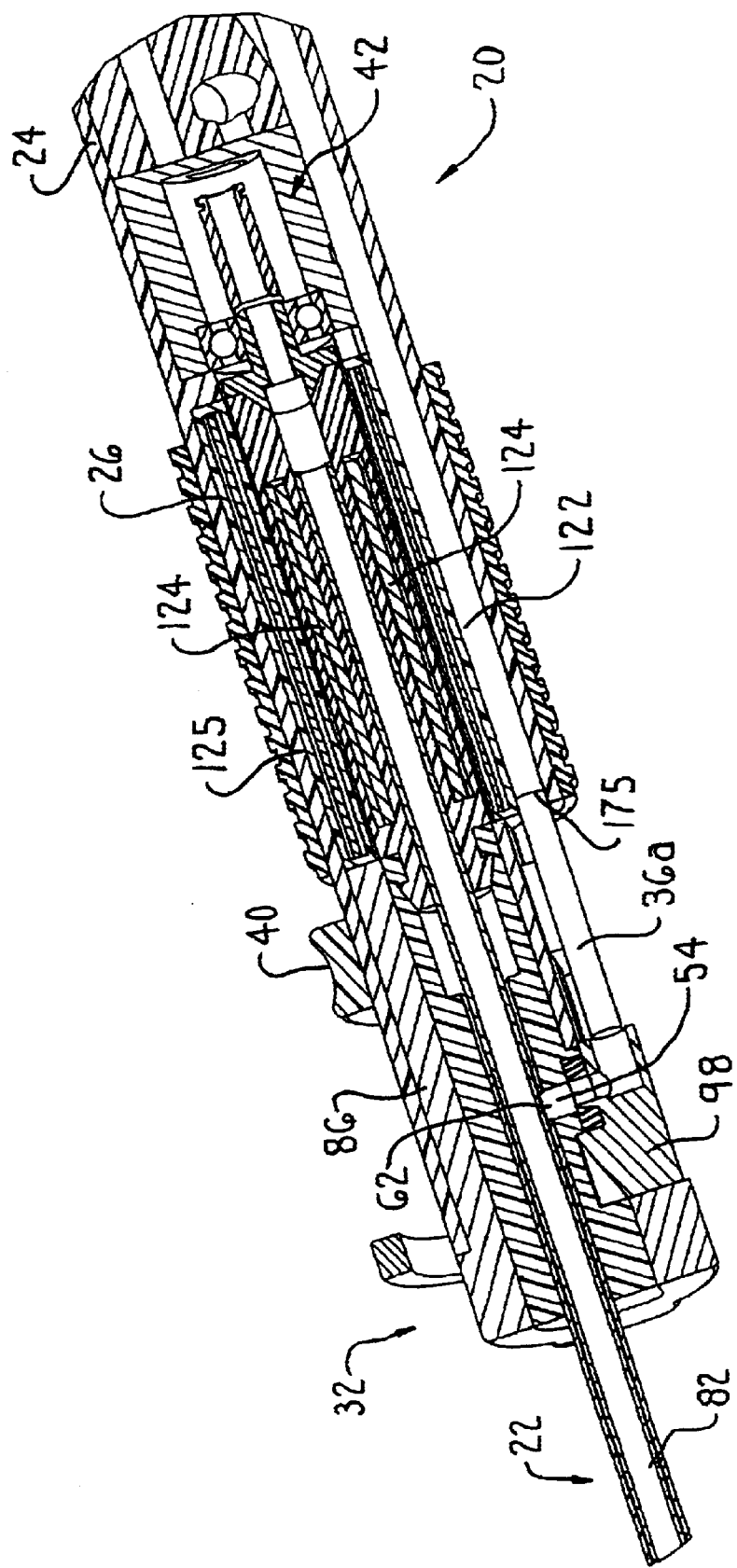
FIG. 2 is a cross sectional view of the distal end of the handpiece as well as of the portion of the cutting accessory seated in the handpiece.

FIGS. 1 and 2 depict a powered surgical handpiece 20 of this invention along with a cutting accessory 22 that is driven by the handpiece. The handpiece 20 has a generally cylindrical sleeve-like shell 24 that serves as the housing for the other components of the handpiece. The proximal end of the cutting accessory 22 is also seated in shell 24. (Hereinafter "front", "forward" and "distal" shall be understood to means portions of the handpiece 20 or cutting accessory 22 located towards the end of the cutting accessory applied to the surgical site. "Rear", "rearward" and "proximal" shall be understood to be portions of the handpiece 20 and cutting accessory 22 located away from the end of the cutting accessory applied to the surgical site.) Collectively, the handpiece 20 and cutting accessory 22 are provided with components that form a motor 26 for actuating the cutting accessory 22. The energization signals that are applied to the motor 26 are generated by a control console 28 and applied to the motor over a power cable 30. One such control console 28 that can be employed to generate the energization signals is the TPS™ control console manufactured by the Applicant's Assignee. A switch assembly, such as a foot switch, not illustrated and not part of this invention, is used for regulating the actuation of the handpiece motor 26. This switch assembly is connected to the control console 28. Based on the signals generated by the switch assembly, the control console 28 applies the energization signals to the handpiece motor 26.

The handpiece 20 includes a coupling assembly 32 that releasably holds the cutting accessory 22 to the handpiece. An irrigation pump 34 applies an irrigation fluid to a supply line 36 that is fitted in shell 24. The irrigation fluid is introduced into the cutting accessory 22 for application to the surgical site through the coupling assembly 32. In the preferred version of the invention, irrigation pump 34 is a module built into and regulated by the control console 28.

A suction is drawn from the surgical site through the cutting accessory 22 and handpiece 20 by a suction pump 38. A manually-set slide lever 40 extends around the outside of the shell 24 and is located immediately rearward of the coupling assembly 32. Slide lever 40 sets the position of a valve member 42 internal to the handpiece 20 which regulates fluid flow through a suction conduit integral with the cutting accessory 22. Depending on the position of the valve member 42, suction pump 38 may draw a suction through the conduit, the suction flow may be attenuated, the suction flow may be completely shut off or the flow from irrigation pump 34 may be directed through the cutting accessory suction conduit.

Figure 3:
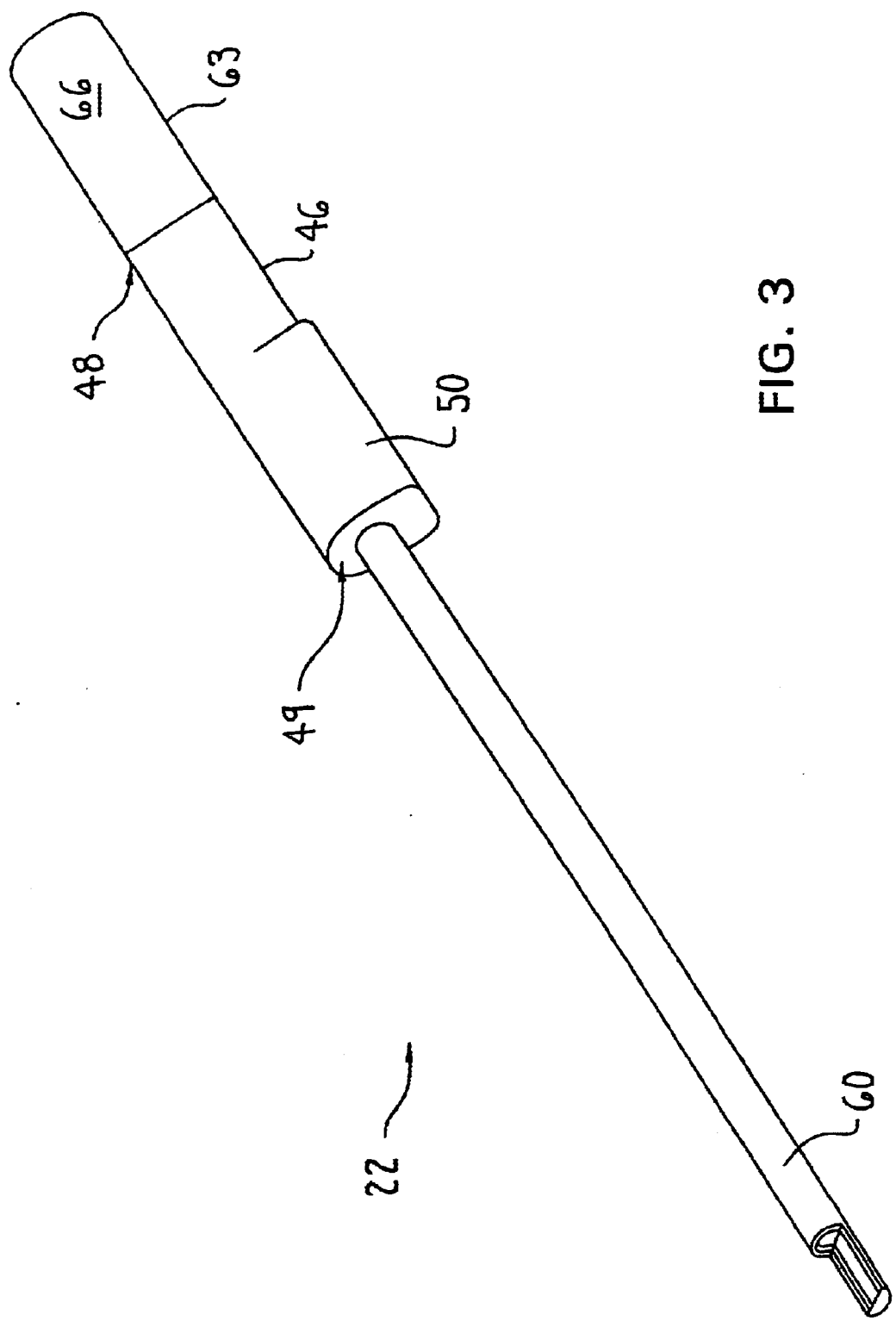
FIG. 3 is a perspective view of the cutting accessory.

The cutting accessory 22, now described by reference to FIGS. 3 and 4, includes a static hub 46 formed of plastic such as a polycarbonate plastic. Static hub 46 has a proximal end 48 with a circular cross sectional profile. The static hub 46 has a distal end 49 formed integrally with the proximal end 48, that has a cross sectional profile that is at least partially asymmetric relative to the longitudinal axis of the hub. In the depicted version of the invention, this static hub distal end 49 is formed so that one surface thereof has a round profile and the opposed surface is shaped to define an alignment key 50. The alignment key 50 projects beyond the circle defined by the proximal end 48 of the hub 46 and is shaped to have a flat outer surface. A through bore 47 extends axially through static hub 46 from the proximal end 48 to the distal end 49.

The static hub 46 is further formed to have a rectangular notch 52 that extends inwardly from the flat surface of the alignment key 50. As discussed hereinafter, a complementary component of the handpiece coupling assembly 32 seats in notch 52 to hold the cutting accessory 22 to the handpiece 20. A fluid inlet bore 54 extends perpendicularly relative to the longitudinal axis of accessory 22 from the alignment key 50 to through bore 47. Fluid inlet bore 54 serves as the conduit through which irrigation fluid is introduced into the cutting accessory 22 from supply line 36. In the depicted version of the invention, an irrigation seal 56 formed from a soft rubber such as is sold under the trademark VITON by the duPont Company of Delaware is seated around the open end of fluid inlet bore 54. Irrigation seal 56 is seated in a cutaway space 58 integral with notch 52. Seal 56 is shaped so that the outer surface thereof is flush with the outer flat surface of the alignment key 50.

A rigid, outer tube 60 formed of stainless steel is firmly connected to the static hub 46 and extends forward from the distal end of the through bore 47. In the depicted version of the invention, the outer tube 60 is shown as having a closed distal end though that not may always be the case. (The distal end of the outer tube 60 is the end of the tube applied to the surgical site.) Outer tube 60 is formed to have a fluid inlet opening 62 that is concentric with and has the same radius as fluid inlet bore 54.

Cutting accessory 22 also has a rotating hub 63 that is located rearward of static hub 46. Rotating hub 63 is formed from a plastic such as polycarbonate plastic. The rotating hub 63 has a main body 66 that is located immediately rearward of proximal end 48 of static hub 46. In the depicted version of the invention, the cross sectional profile of rotating hub 63 is identical to that of the adjacent static hub proximal end 48.

The rotating hub 63 is formed to have a neck 68 and a head 70 that extend forward from the main body 66 into the static hub proximal end 48. More specifically, neck 68 extends forward from body 66 and has a constant diameter cross section profile less than the diameter of the main body. Head 70 is shaped to have a tapered profile such that the portion of the head immediately adjacent neck 68 has a diameter greater than that of the neck and the most distal end of the head has a cross-section diameter approximately equal to the diameter of the neck. The neck 68 and head 70 are seated in complementary shaped bores 72 and 74, respectively, formed in the static hub proximal end 48. Bores 72 and 74, it will be observed, surround and are contiguous with through bore 47. More specifically, the hubs 46 and hub 63 are formed so that there is an interstitial gap between the outer surfaces of neck 68 and head 70 and the inner surfaces of the static hub 46 that define bores 72 and 74. In preferred versions of the invention, this annular gap, not identified, is between 20 and 25 mils (0.5 and 0.7 mm). This gap reduces friction between the interface of the neck 68 and head 70 and the static hub 46.

Rotating hub 63 is further formed with an axially extending through bore 76 that is concentric with the static hub through bore 47. An outwardly tapered counterbore 78 is formed with through bore 76 at the proximal end of the rotating hub 63.

A rotating inner tube 79 is securely mounted to the inner wall that defines through bore 76 in order to turn in unison with rotating hub 63. Inner tube 79 extends forward from the distal end of rotating hub 63 into the center of outer tube 60. The distal end of inner tube 79 is formed to serve as a cutting head. In the depicted versions of the invention, the distal end of the inner tube 79 is open and has sharp edges so that this end of the tube functions as a planar. It should, of course, be recognized that different heads may be attached to the distal end of the inner tube so that the cutting accessory 22 may serve as a burr, a shaver, a resector or other cutting device.

It should be realized that when the cutting accessory 22 is a cutter or a shaver, the distal end of the static outer tube 60 is closed. In these cutting accessories 22, the distal end of the inner tube 79 is dimensioned to abut against the inner wall of the closed distal end of the outer tube 60. Thus, the inner tube 79 holds the main body 66 and head of the rotating hub 63 away from, respectively, the distal end of the static hub 46 and the inner wall of the static hub that defines bore 74. This holding off of the rotating hub 63 from the adjacent surfaces of the static hub 46 as well as the fact that neck 68 is spaced inwardly from the walls defining bore 72 serves to substantially eliminate frictional between the hubs.

Outer and inner tubes 60 and 79, respectively, are further dimensioned so that there is a small annular channel 81 between the outer wall of the inner tube 79 and the adjacent inner wall of the outer tube 60. Annular channel 81 serves as the conduit through which irrigation fluid flows from the fluid inlet bore 54 and the fluid inlet opening 62 to the surgical site. The hollow center of inner tube 79 serves as a conduit 82 through which a suction is applied to the surgical site for drawing fluid and debris away from the site.

Figure 5:
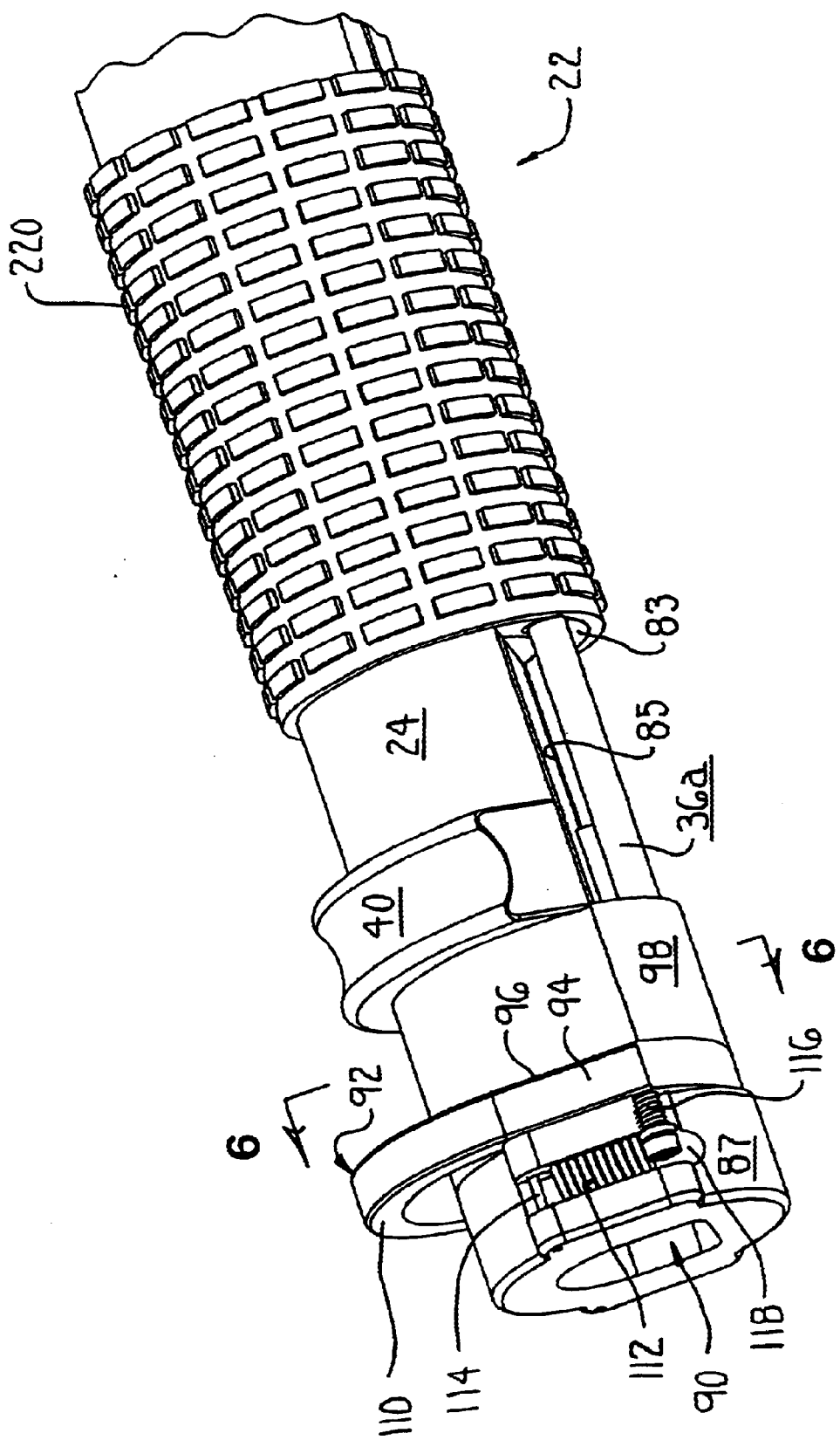
FIG. 5 is a enlarged view of the distal end of the handpiece.
Figure 6:
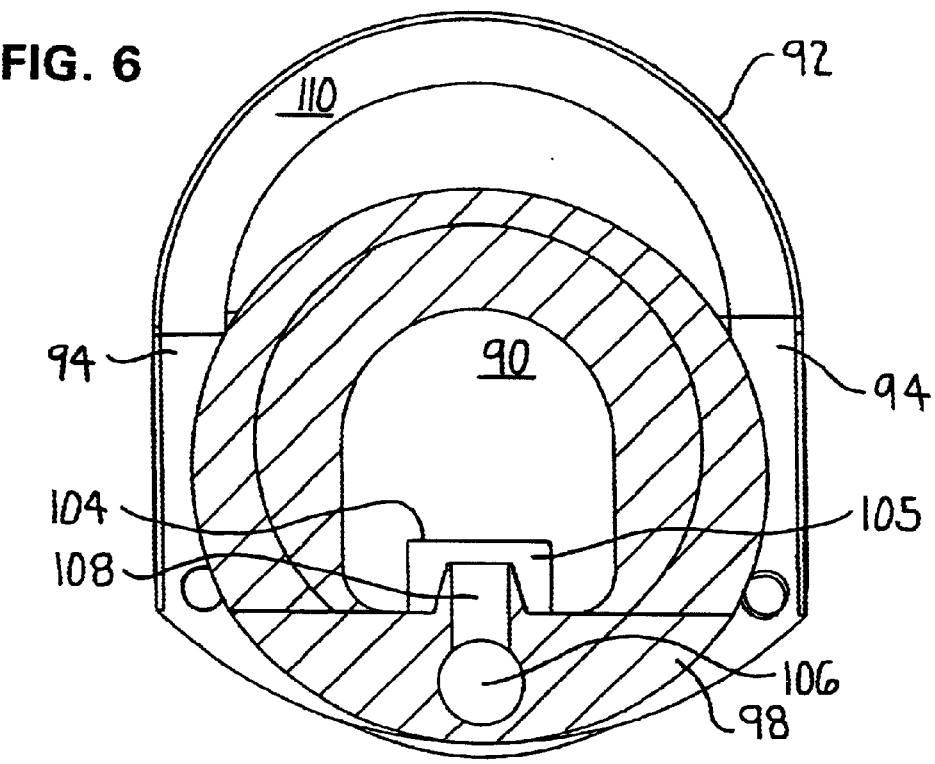
FIG. 6 is a section view of a lateral slice of the handpiece taken along line 6—6 of FIG. 5.

The handpiece 20 is now described in detail with an initial discussion of the construction of the coupling assembly 32, best seen by reference to FIGS. 2, 5 and 6. The front end of the handpiece 20 is provided with a solid coupling body 86 formed of PEEK plastic that is seated in the front end of shell 24. More specifically, in the depicted version of the invention, the forward end of shell 24, is shaped to subtend an arc of approximately 200 to 260°. Immediately rearward of this section of the shell 24, the shell is shaped to have a forward-directed front plate 83.

The section of coupling body 86 seated in shell 24 thus has an exposed outer surface 85. The coupling body 86 is further shaped to have a head section 87 that extends forward of shell 24. Head section 87 has a cross-sectional profile that is approximately equal to that of the adjacent end of the shell 24 from which the head extends. Coupling body 86 has an axially extending bore 88 dimensioned to receive static hub 46. The coupling body 86 is formed so that bore 88 has a distal opening 90 with a cross-sectional profile identical to that of the static hub distal end 49, including the alignment key 50. This configuration insures that the static hub 46 seats in coupling body 86 in a specific orientation for purposes to be explained below.

The coupling assembly 32 also includes an oval-shaped coupler arm 92. The arm 92 is slidably mounted to the outside of coupler body 86 so as to move perpendicularly relative to the longitudinal axis of the handpiece 20. Coupler arm 92 has two parallel, spaced apart links 94 each of which is seated in a separate slot 96 formed by an interstitial space between the distal end of the shell 24 and the proximal end of the coupler body head section 87. Links 94 are connected together at one end by a locking member 98. The locking member 98 is positioned adjacent an opening 102 in the exposed surface 85 of the coupler body 86 rearward of head section 87. Opening 102 extends into the distal section 90 of bore 88. The locking member 98 is formed to have a tab 104 that extends through opening 102 into bore 88. Tab 104 is the component of the coupling assembly 32 that seats in notch 52 to hold the cutting accessory 22 to the handpiece 20. The tab 104 is formed with a forward facing surface 105 that is angled rearwardly to facilitate the fitting of the cutting accessory 22 to the handpiece 20.

Irrigation fluid is introduced into the cutting accessory 22 through the coupler arm 92. Specifically, the distal end of the supply line, distal supply line 36a in the drawings, is fitted into a rearward facing bore 106 formed in locking member 98. Locking member 98 has a cylindrical outlet fitting 108 that is in fluid communication with bore 106 and is directed inwardly towards the longitudinal axis of the handpiece 20. Outlet fitting 108, which is located rearward of tab 104, is positioned so that when the tab 104 seats in the cutting accessory notch 52, the fitting 108 seats in the opening integral with irrigation seal 56. Thus, when the cutting accessory 22 is mounted to the handpiece 20, fluid flows from the supply lines 36 and 36a through bore 106 and fitting 108, into accessory inlet bore 54, inlet opening 62 and channel 81 to the surgical site.

The ends of links 94 distal from locking member 98 are connected together by a semi-circular web 110. Two springs 112 bias coupler arm 92 so that tab 104 is normally urged into bore 88. The springs 112, which are parallel to each other, are connected at one end to separate posts 114 fitted in coupler body head section 87. The opposed end of each spring 112 is connected to a small set screw 116 that extends forward from an adjacent one of the links 94. The coupler body head section 87 is further formed to have opposed grooves 118 in which each spring 112 is seated. Since the springs 112 are seated in grooves 118, the likelihood of an individual inadvertently disturbing a spring or finger or an article of clothing becoming caught in one of the springs is substantially eliminated.

Figure 2A:
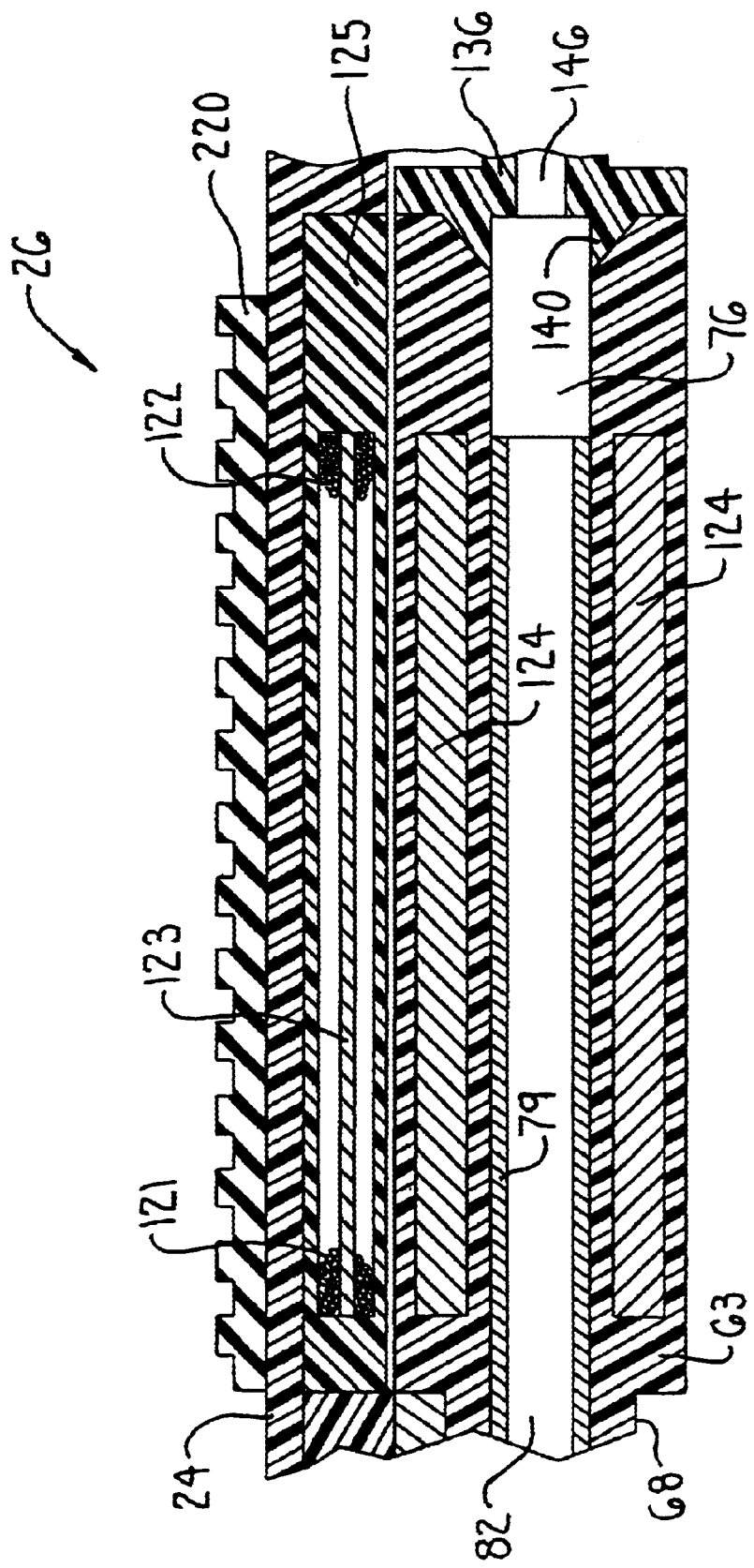
FIG. 2A is a detailed cross sectional view of the motor depicted in FIG. 2.
Figure 4:
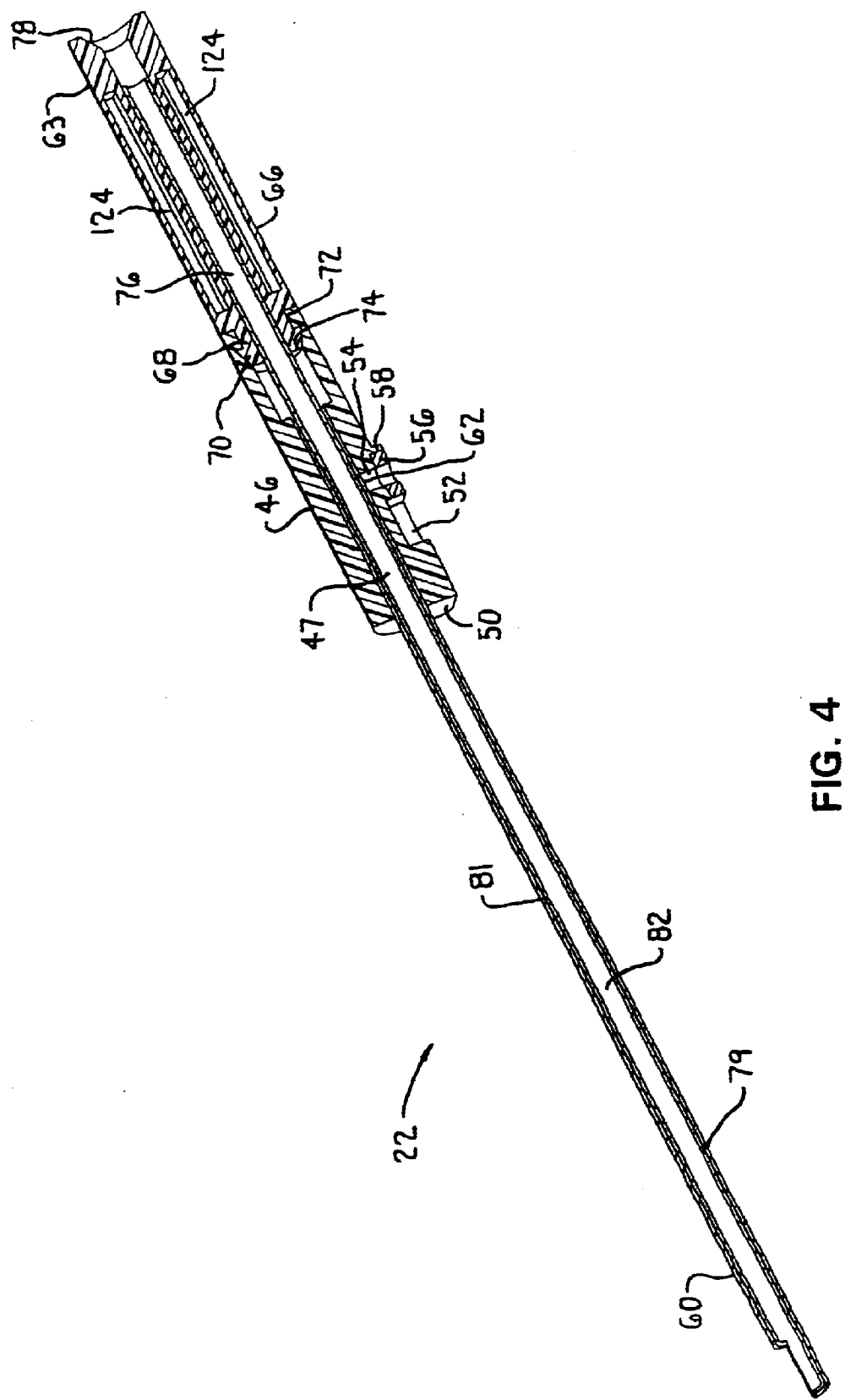
FIG. 4 is a cross sectional view of the cutting accessory.
Figure 7:
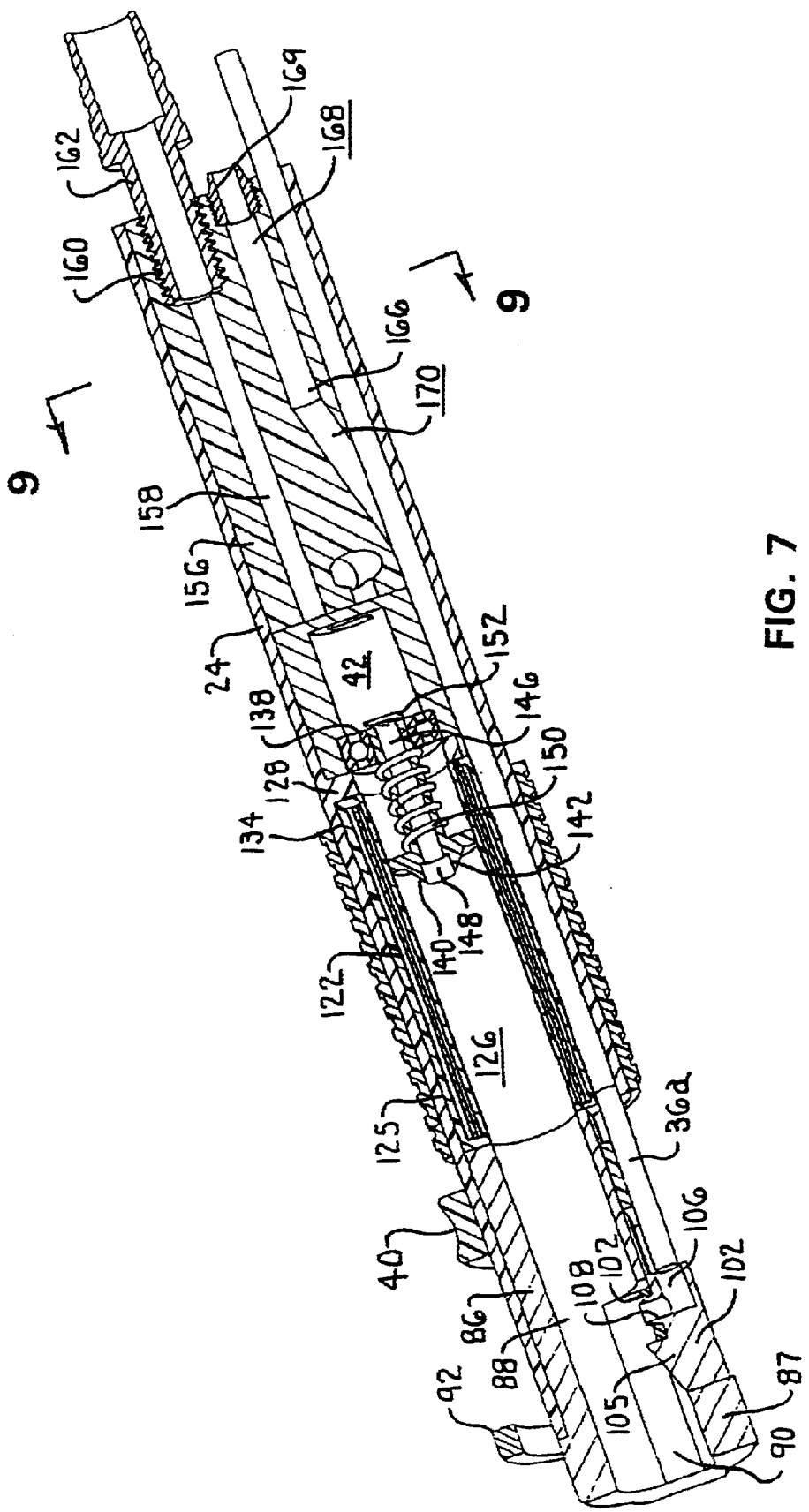
FIG. 7 is a cross sectional view of the inside of the handpiece.

The motor 26 seen best in FIGS. 2 and 2A, includes a stator 122 that is mounted in the shell 24 and a set of magnets 124 that are disposed in the cutting accessory rotating hub 63 as seen in FIGS. 2, 4 and 7. In one preferred version of the invention, the motor is a four-pole, three-phase brushless, sensorless DC motor. More specifically, the stator 122 includes a set of three windings 121 that are wound around a cage 123. Electrically, the windings are 120° apart from each other. It should be understood that physically, the windings may overlap. The stator 122 is encased in an insulating shell 125 that is formed from non-conductive material such as PEEK plastic. Shell 125 is shaped so as to define an axially extending center space 126 in which the cutting accessory rotating hub 63 is seated. More particularly, the shell 125 is dimensioned so that there a small air gap between the inner wall of the shell defining space 126 and the outer wall of the rotating hub 63. This air gap is approximately 20 mils, (0.5 mm). This air gap essentially eliminates the rotating friction between the rotating hub 63 and the shell 125.

The rear end of stator shell 125 is seated on an annular step 128 formed integrally with handpiece shell 24. Step 128 extends inwardly from the inner wall of handpiece shell 24 towards the longitudinal center of the handpiece 20.

Since motor 26 is a four-pole motor, four magnets 124 are mounted in the rotating hub. The magnets 124 are elongated members that are spaced equangularly around the longitudinal axis of the cutting accessory 22. The magnets are formed so that their N/S polar orientation is located along an axis perpendicular to the longitudinal axis of the cutting accessory 22. Thus, for a first one of the magnets 124, the North pole is oriented towards the center of the rotating hub. The magnets 124 adjacent the first magnet are arranged so that their South poles are oriented towards the center of the rotating hub.

The magnets 124 may have a cross sectional profile that is either curved or squared. Alternatively, the magnets may even have arcuate cross sectional profile. In these versions of the magnets 124, the outer face of each magnet may have a convex profile having a first radius while the inner face of the magnet has a concave profile with a radius less than that of the first radius. The magnets 124 may be made out of any appropriate material such as samarium cobalt.

A plunger 134 is seated in the rearward portion of stator 122. The plunger 134 is formed from stainless steel. The plunger 134 has a cylindrical stem 136. Stem 136 is mounted in a plunger bearing assembly 138. The plunger bearing assembly 138 is seated in the front end of the valve member 42 as will be described hereinafter. Plunger 134 is further formed with a head 140 that is formed integrally with and has a larger cross sectional diameter than the stem 136. In the depicted version of the invention, plunger head 140 is dimensioned so that it comes close to, but does not abut the adjacent inner wall of the stator 122. The plunger head 140 has a center section 142 that extends forward from the outer perimeter of the head. The center section 142 of the plunger head 140 seats in counterbore 78 formed in the proximal end of rotating hub 63.

A bore 146 extends axially through plunger 134 from the proximal end of the plunger to the distal end. Bore 146 serves as a conduit through which fluid flows between valve member 42 and rotating hub bore 76. In the depicted version of the invention, the plunger head 140 has a counterbore 148, concentric with bore 146, that has the same diameter as the rotating hub bore 76.

A coil spring 150 is disposed around plunger stem 136 and extends between plunger bearing 138 and the rearward facing surface of plunger head 140. Spring 150 provides the biasing force that urges the plunger 134 forward so that the plunger imparts a like force to cutting accessory 22. A retaining ring 152 fitted in a groove extending around the end of stem 136 seated within the valve member 42 (groove not identified). Retaining ring 152 abuts against the rearward facing surface of plunger bearing assembly 138 to prevent the plunger 134 from separating from the bearing assembly 138.

Figure 9:
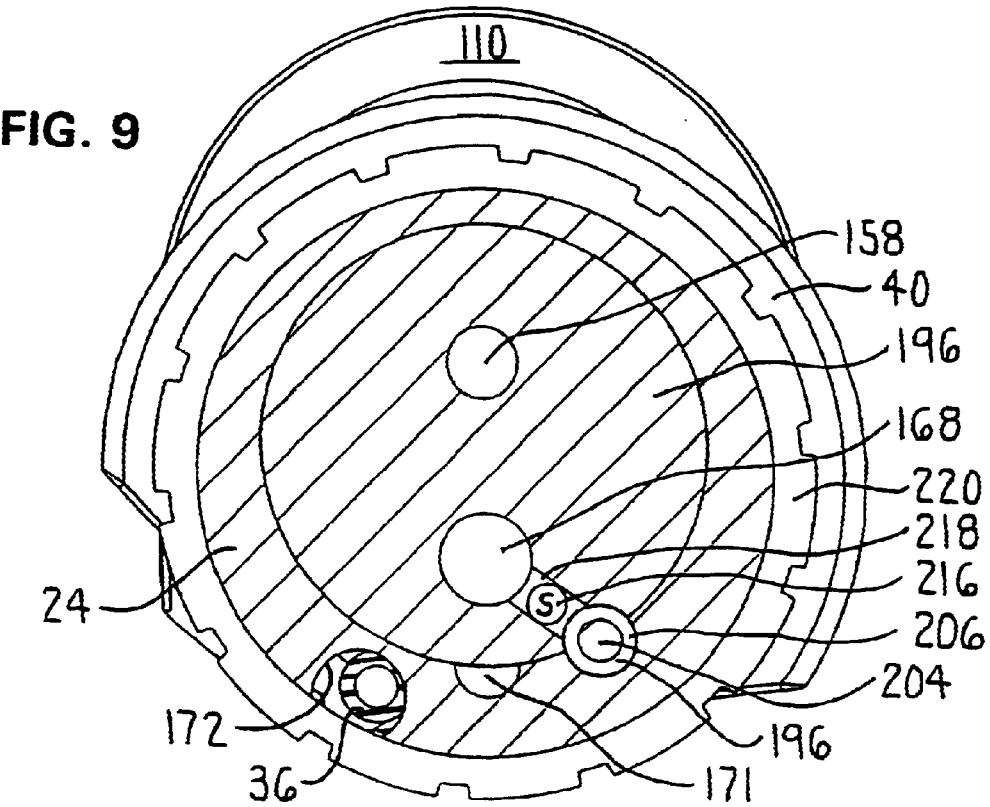
FIG. 9 is a section view of a lateral slice of the handpiece taken along line 9—9 of FIG. 7.
Figure 8:
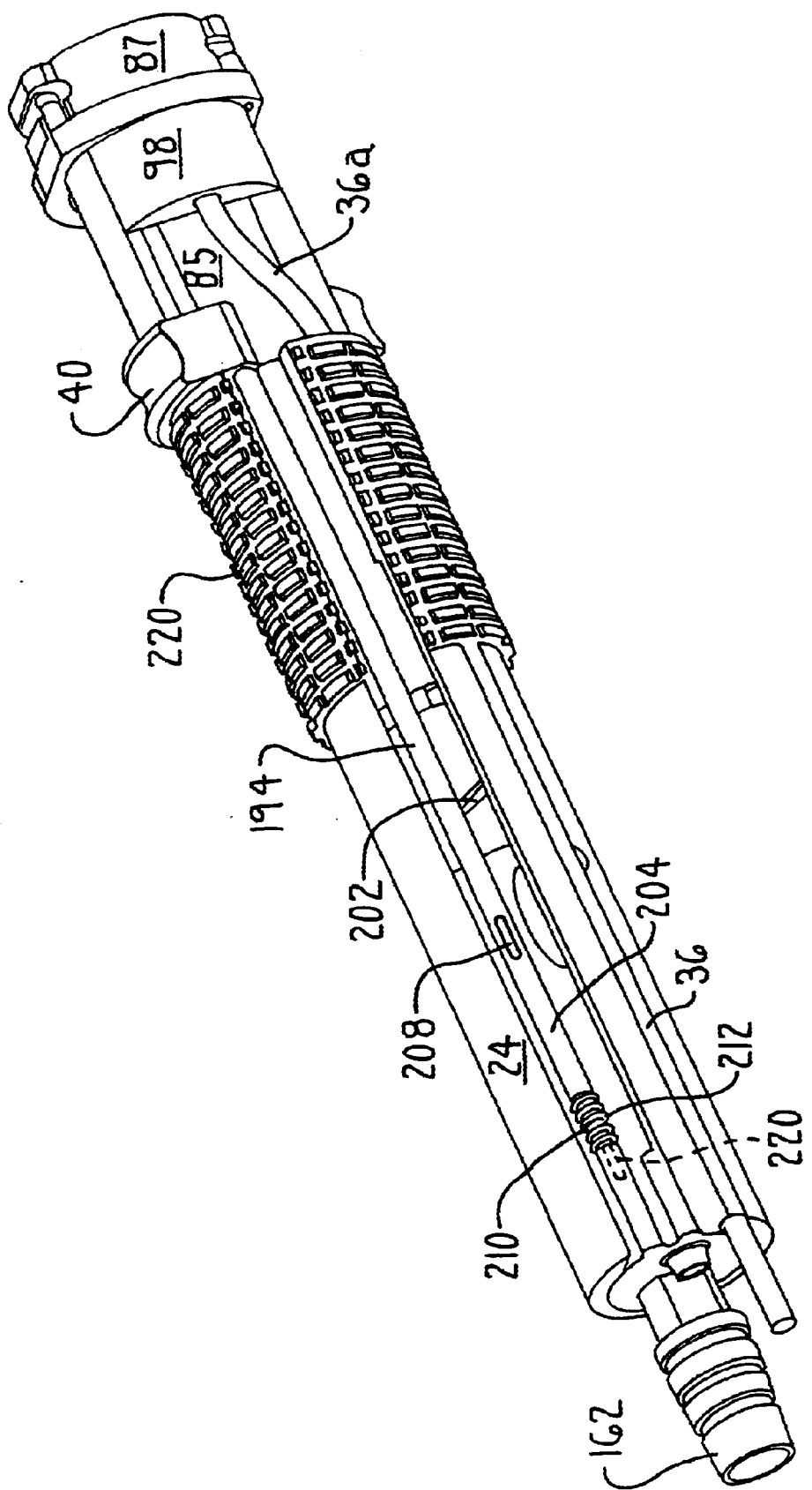
FIG. 8 is a perspective cutaway view of the handpiece.

An explanation of how fluid is selectively introduced into and drawn from conduit 82 of cutting accessory 22 through the handpiece 20 of this invention is now set forth with initial reference to FIGS. 7–9. As seen in these drawings, a solid, cylindrical end cap 156 formed of PEEK plastic is seated in the proximal end of shell 24. End cap 156 is formed with a suction bore 158 that extends laterally through the end cap. It will be observed that suction bore 158 is laterally offset from the longitudinal axis of the end cap 156. Suction bore 158 is formed to have a threaded counterbore 160 which is located at the proximal end of the end cap 156. A luer fitting 162 is seated in suction bore counterbore 160. The luer fitting 162 serves as a means to connect a suction line 164 between the suction bore 158 and suction pump 38. The opposed end of suction bore 158 defines an opening 165 in the distal end face of end cap 156.

End cap 156 is also formed to have a supplemental conduit 166. The supplemental conduit 166 serves as the conduit in which the electrical conductors integral with the handpiece 20 are seated (conductors not illustrated). The supplemental conduit 166 extends forward from the proximal end of the end cap 156. In the depicted version of the invention, end cap 156 is formed so that supplemental conduit 166 is laterally offset from the longitudinal axis of the handpiece 20. Supplemental conduit 166 has two sections. There is a proximal section 168 in which the conduit is essentially parallel to the suction 158. There is also a distal section 170 that is contiguous with and extends forward from proximal section 168. Distal section 170 angles away from proximal section 168 and opens in the side of the end cap 156 at a point rearward of the distal end of the end cap. The conductors extend out of the end of the opening of supplemental conduit distal section 170 and seat in a groove 171 formed on the inner wall of shell 24 (FIG. 9). The conductors extend from the shell 24 to the stator 122 to provide energization signals to motor 26. A tube-shaped ferule 169 extends rearwardly from the open proximal end of the supplemental conduit 166. Ferule 169 protects the end of the cable 30 that extends into the conduit 166.

Figure 10:
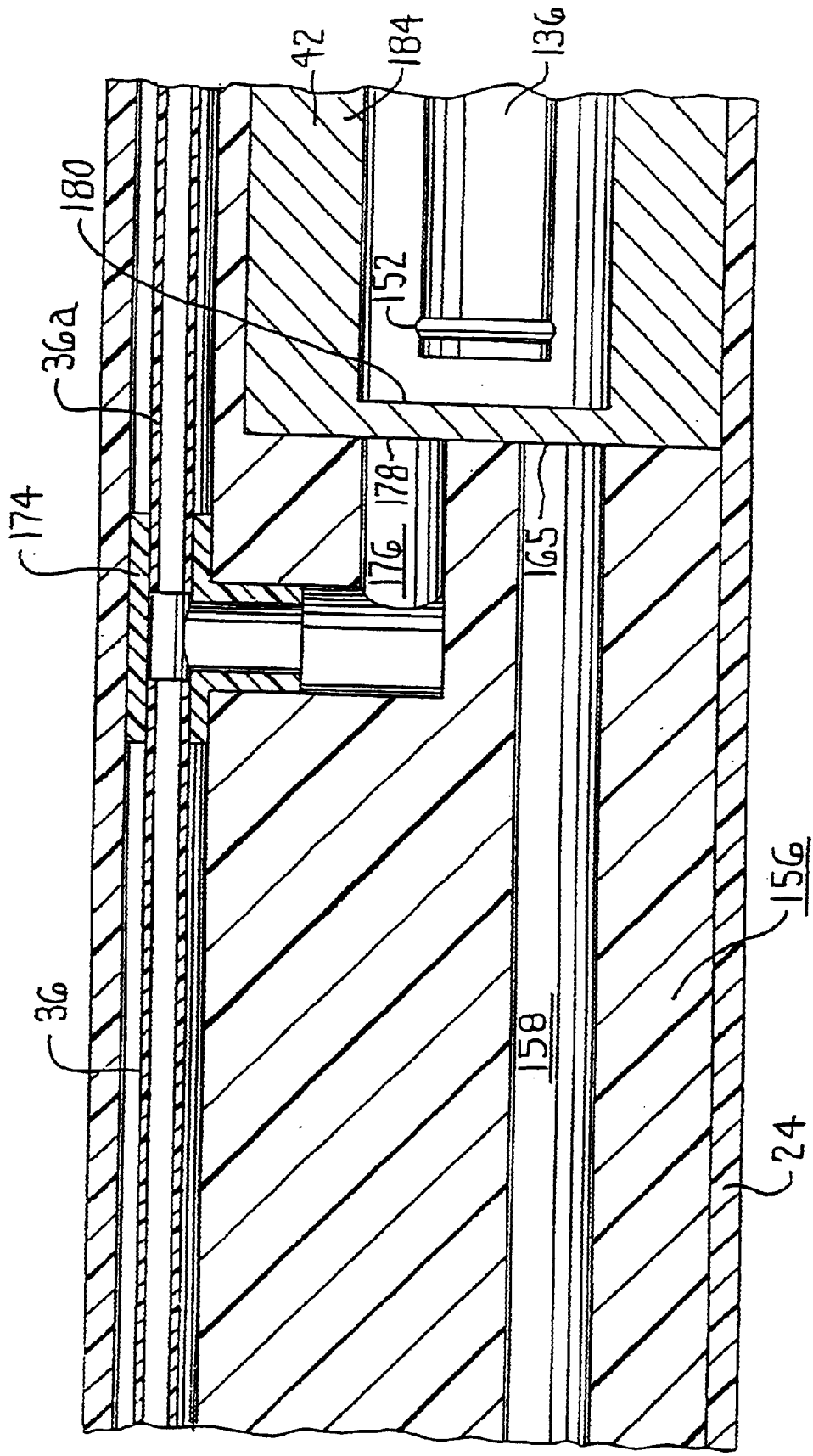
FIG. 10 is a cross sectional view of the inside of the handpiece depicting the fluid conduits in the end cap that lead to and from the valve member.

The irrigation fluid supply line 36 is fitted in a groove 172 that extends longitudinally along the outside of shell 24 seen best by reference to FIGS. 2, 5 and 10. Supply line 36 terminates at one end of a T-connector 174 mounted to the end cap. Distal supply line 36a extends from the opposed end of T-connector 174 into the bore 106 associated with coupler arm 92. More specifically, groove 172 extends forward a short distance from T-connector 174 and distal supply line 36a is seated in the groove. Distal supply line 36a extends through groove 172 and out through an opening 175 in the shell front plate 83. The forward end of the distal supply line 36a is the end of the line fitted to coupling arm bore 106.

Focusing on FIG. 10, it can be seen that the center stem of T-connector 174 is mounted in an L-shaped irrigation bore 176 formed in the distal end of end cap 156. Bore 176 has an opening 178 in the distal end face of the end cap 156.

Figure 11:
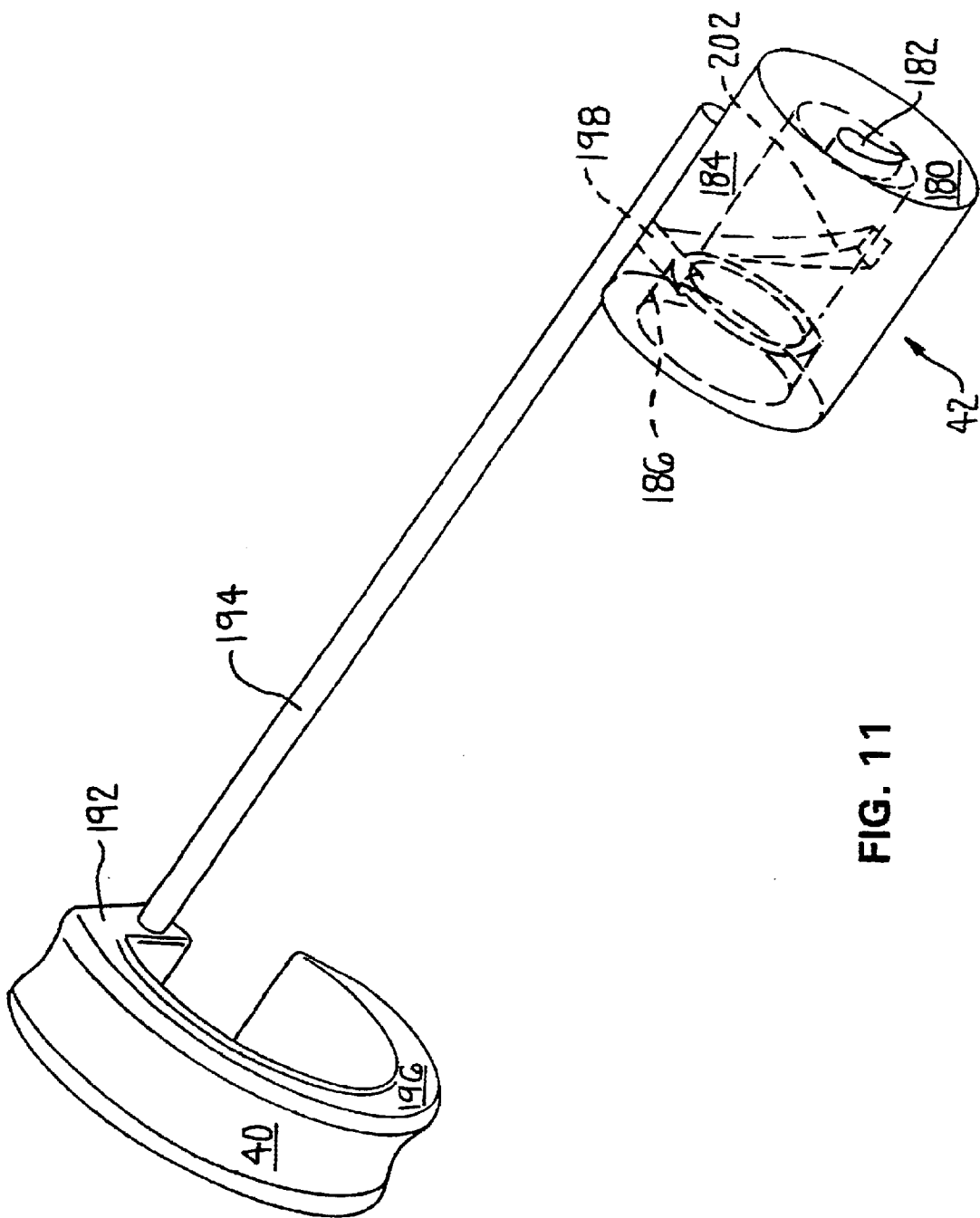
FIG. 11 is a perspective view depicting the relationship of the slide lever, the slide rod and valve member.

Valve member 42, now described by reference to FIGS. 7 and 11, is shaped to have a generally cylindrical shape. The valve member 42 has a circular, disc-like base 180 that abuts the distal end face of end cap 156. This space forward of end cap 156 is the valve chamber 179 of handpiece 20. Valve member base 180 has a tear-dropped shaped opening 182 that, depending on the position of the valve member 42, is selectively positioned to be in registration with suction bore opening 165 or irrigation bore opening 178. The valve member 42 is further formed to have tube-like body 184 that extends forward from the distal end of base 180. The body 184 is the portion of the valve member 42 to which plunger bearing assembly 138 is mated and in which the plunger stem 136 extends. More specifically, the inner wall of valve member body 184 is formed to define an annular step 186 in which the plunger bearing assembly 138 is seated.

The setting of valve member 42 is controlled by slide lever 40. The slide lever 40 has a curved section 190 that fits around the portion of shell 24 that surrounds coupler body 86. Slide lever 40 also has a flat section 192 integral with the curved section 190 that is located against the exposed surface 85 of the coupler body below coupler arm 92. A slide rod 194 extends rearwardly from slide lever flat section 192. Slide rod 194 is seated in a longitudinally extending groove 196 formed on the inside wall of shell 24. In order to ensure that the slide rod seats in groove 196, the rod is formed to have a semi-circular cross sectional profile.

Slide rod 194 is provided with a pin 198 (Shown in phantom) that extends inwardly towards the longitudinal axis of the handpiece 20. Pin 198 seats in a helical groove 202 (Shown in phantom) formed in the outer surface of valve member body 184. Thus, the forward/rearward displacement of slide lever 40 and slide rod 194 control the rotational position of valve member 42.

An extension rod 204, seen in FIGS. 8 and 9, is attached to the proximal end of slide rod 194 to move with the slide rod. Extension rod 204 has a generally circular cross sectional profile. The outer half of extension rod 204 seats in shell groove 196. The inner half of extension rod 204 seats in a groove 206 formed along the outer wall of end cap 156. A small magnet 208 is mounted in an opening in extension rod located adjacent the distal end of the rod 204 (opening not identified).

Extension rod 204 is shaped to have a reduced diameter pin 210 that extends rearwardly from the proximal end of the rod 204. Pin 210 seats in a forward-facing bore 220 (shown in phantom) formed in the proximal end of end cap 156. A spring 212 extends around pin 210. Spring 212 provides a biasing force that push extension rod 204, slide rod 194 and slide valve 40 forward. Thus, slide valve 40 is normally positioned to be located immediately rearward of locking member 98.

A reed switch 216, or other sensor, is seated in the end cap 156 to monitor the displacement of magnet 208. In the depicted version of the invention, reed switch 216 is mounted in a branch channel 218 that extends laterally away from the proximal section 168 of supplemental conduit 166. The signal across the reed switch is monitored by a circuit internal to control console 28. The electrical conductors (not illustrated) that extend to reed switch 216 are fitted in conduit 166. Also, in the depicted version of the invention, branch channel extends to groove 206 though this need not always be the case. The open/closed state of reed switch 216 is monitored by a controller internal to irrigation pump 34.

A tube-like handgrip 220 formed of rubber surrounds shell 24. The handgrip 220 surrounds the portion of the shell that extends rearward from plate 83.

The handpiece 20 of this invention is readied for use by the fitting of the cutting accessory 22 to the handpiece. This is performed by inserting the accessory hubs 46 and 63 into the open end of handpiece bore 88. When the static hub alignment key 50 seats in the bore distal opening 90, the flat face of the key abuts against the angled forward facing surface 105 of tab 104. Owing to the angle of surface 105, this action causes the tab 104 to automatically retract away from bore 88 so that the cutting accessory 22 can continue to be fitted in place. Once notch 52 of static hub 46 comes in registration with tab 104, springs 112 urge locking member 98 towards the center axis of the handpiece so that the tab seats in the notch. The seating of the tab 104 in notch 52 locks the cutting accessory 22 in place.

Simultaneously with the seating of tab 104 in notch 52, outlet fitting 108 comes into registration with accessory inlet bore 54. Thus, the locking of the cutting accessory 22 to the handpiece 20 of this invention results in the automatic establishment of a path through which irrigation fluid can flow through supply lines 36 and 36a into the annular channel 81 of cutting accessory 22. Thus, once the coupling accessory 22 is fitted to the handpiece 20 additional time need not be spent establishing this fluid connection.

It should also be understood that when irrigation fluid is introduced into the inlet bore 54, the fluid does not flow rearward beyond the interface of the static hub 46 and rotating hub 63. This is because the pressure head of the fluid is not sufficient to force the fluid between the narrow gap between the hubs 46 and 63.

When it is necessary to remove the cutting accessory 22 from the handpiece 20, all one needs to do is manually urge coupler arm web 110 inwardly towards shell 24. This action causes tab 104 to retract away from cutting accessory notch 52. Simultaneously with the retraction of tab 104, outlet fitting 108 retracts away from bore 54. Once the tab 104 is moved away from notch 52, cutting accessory 22 can be manually removed from bore 88. The removal of the cutting accessory 22 is facilitated by the fact that, once the tab 104 is so retracted, the force of the plunger spring 150 is fully released. Thus, the spring 150 pushes the plunger 136 forward so the plunger causes a like displacement of the cutting accessory 22 out of the forward end of the handpiece 20.

The cutting accessory 22 is actuated by selectively applying energization currents to the windings integral with the stator 122. These currents cause magnetic fields to develop which attract the magnets 124 internal to rotation hub 63. The attraction of the magnets 124 to the windings causes rotation of hub 63 as well as inner tube 79 integrally attached thereto. Plunger 134, which is pressed against rotating hub 63, rotates with the hub. An advantage of this arrangement is that in this construction only the single bearing assembly 138 is required to insure the free rotation of rotor that is integral with the motor. Moreover, since the windings and magnets 124 are contained in their own sealed housings, and there are no bearings, it is not necessary to provide a separate sealed housing for the motor 26. Two advantages of this construction are that it eliminates both the cost and weight of having to provide a sealed housing. Still another benefit of this feature of the invention is that the motor 26 of this handpiece 20 does not have any metal components that are exposed to fluid in the event a seal wears or breaks. Thus, there is little likelihood that the motor of this invention will malfunction due to corrosion-induced component failure.

Figure 12:
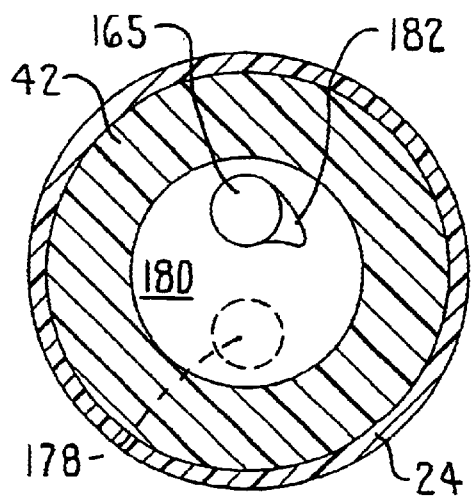
FIG. 12 is a plan view of the relative position of the valve member and the associated conduits with the valve member is in the suction full on state.

The handpiece 20 of this invention is further configured to regulate whether or not a suction is drawn through or irrigation fluid is applied to conduit 82 integral with the cutting accessory inner tube 79. During normal operation of the handpiece 20, valve member 42 has the rotational orientation depicted in FIG. 12. Here, the valve member 42 is positioned so that the largest diameter section of base opening 182 is in registration with opening 165 integral with suction bore 158. Thus, when the valve member 42 is in this position, the maximum possible suction is drawn from the surgical site through inner tube conduit 82, rotating hub bore 76, plunger bore 146 and the suction bore by suction pump 38. Further, when the valve member 42 is in this position, base 180 covers and closes irrigation bore opening 178. The sealing closed of opening 178 prevents irrigation fluid from being introduced into the center of the valve member when the suction is being drawn.

Figure 13:
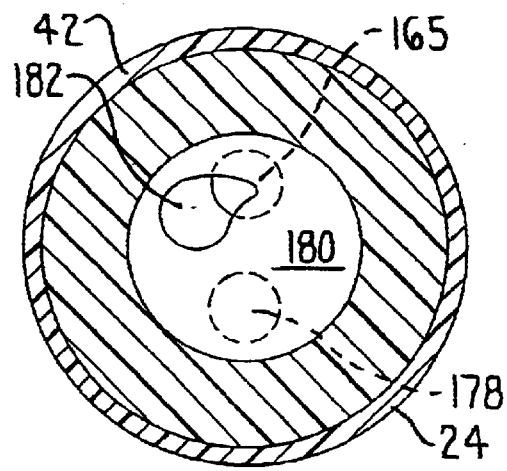
FIG. 13 is a plan view of the relative position of the valve member and the associated conduits when the valve member is in the suction partial on state.

A surgeon attenuates the suction drawn at the surgical site by moving slide lever 40 rearward towards handgrip 220. This motion causes a like displacement of slide rod 194. The displacement of slide rod 194 causes valve member 42 to rotate first to the position depicted in FIG. 13. When the valve member 42 is in this position, the narrow diameter section of valve member base opening 182 is in registration with suction bore opening 165. Thus, at this time, a reduced volume suction flow is drawn by the pump 38 from the surgical site through the inner tube conduit 82 and the valve member 42.

Figure 14:
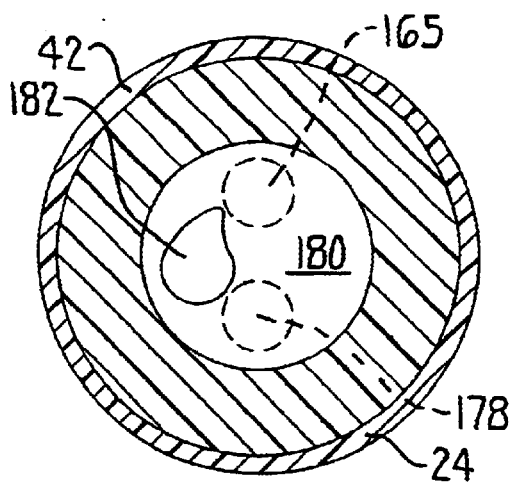
FIG. 14 is a plan view of the relative position of the valve member and the associated conduits when the valve member is in the suction-and-purge off state.

The surgeon may totally turn off the suction drawn at the surgical site by simply moving the slide lever 40 rearwardly. The like movement this induces in the slide rod 194 and pin 198 causes pin to rotate the valve member 42 into the position shown in FIG. 14. When in this state, the valve member 42 covers the both suction bore opening 165 and the irrigation bore opening 178. Thus, at this time, there is no fluid flow in any direction through the inner tube conduit 82 to or from the surgical site.

Figure 15:
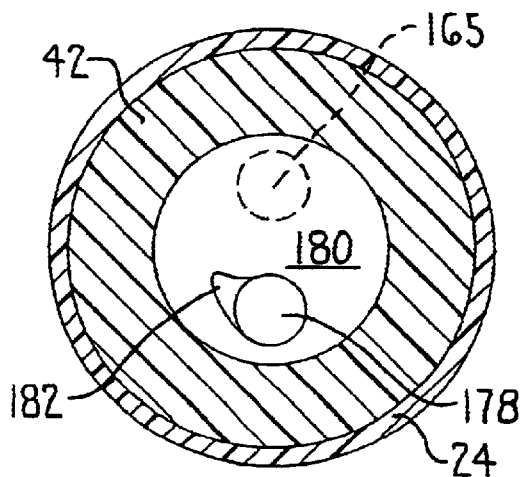
FIG. 15 is a plan view of the relative position of the valve member and the associated conduits when the valve member is in the purge flow on state.

The handpiece 20 of this invention is configured to direct a purge flow through the inner tube conduit 82 in the event the conduit becomes clogged. Specifically, if this event occurs, or for another reason the surgeon wants a very large fluid flow to be introduced into the surgical site, the surgeon presses the slide lever 40 so that the lever is in its most rearward position. This displacement of the slide lever 40 and the associated slide rod 194 results in two effects. First, this displacement causes the valve member 42 to rotate into the position depicted in FIG. 15 in which the large diameter portion of base opening 182 comes into registration with irrigation bore opening 178. Secondly, the magnet 208 that moves with the slide rod 194 moves very close to reed switch 216. This motion causes the reed switch 216 to close so that the signal produced by the switch changes state. This signal change is interpreted by control console 28 as an instruction to boost the rate at which fluid is discharged from the irrigation pump 34. Thus, the moving of the slide valve 40 to the purge position resets the valve member 42 so that irrigation fluid is directed through inner tube conduit 82 and sets the irrigation pump 34 to force a relatively high pressure flow through this conduit. Collectively, this means that when the handpiece 20 is in the purge state, a relatively high pressure stream of fluid is directed through the inner tube conduit 82 towards the surgical site. In many situations, this high pressure fluid stream has enough force to dislodge the debris that are blocking normal suction flow through the inner tube 79.

Thus, the handpiece 20 of this invention provides a means for automatically establishing and breaking an irrigation connection to the cutting accessory 22, has relatively few moving parts and has means to provide a purge flow to the conduit integral with the cutting accessory through which the suction flow is normally drawn.

It should be understood that the foregoing description is directed to one specific embodiment of the invention. It will be apparent, however, from the description that alternative constructions of the invention are possible. For example, not all versions of the invention may have an outlet fitting for providing a fluid communications path to the complementary cutting accessory. Similarly, other versions of the handpiece may not be constructed so that the rotating hub of the cutting accessory forms part of the motor or with a valve member that can be used to introduce a purge flow into the suction conduit integral with the cutting accessory.

For example, it may be desirable to provide a handpiece and complementary cutting attachment of this invention with just the described motor 26. These particular components would thus be designed as tools for conventional surgery in which the handpiece does not also provide irrigation fluid and/or draw suction from the site. Similarly, it may be desirable to provide a handpiece that simply functions as an conduit for supplying irrigation fluid to and/or drawing a suction from the surgical site that has the features of this invention. Specifically, it will be noted that the setting of valve 42 does not effect the always open fluid connection between supply lines 36 and 36a. So when the valve 42 is in the purge position, there is also fluid flow to the surgical site through annular channel 81.

Also, the components from which the handpiece and complementary cutting accessory are formed may have alternative constructions than what has been described. For example, it may be desirable to design the coupling assembly with multiple fingers that are positioned to move towards and away from the cutting accessory. In this version of the invention, the cutting accessory would be formed with recesses in which these fingers seat. The seating of the fingers in these recesses holds the cutting accessory to the handpiece. In these versions of the invention, the inlet fitting may be built into one of the fingers.

It should also be recognized that some versions of the invention, the distal end of the outer tube 60 of the cutting accessory 22 may be open ended. This may be the case when the inner tube 79 is provided with a burr at its head end. In these versions of the invention, the tubes cannot be configured to hold the rotating hub 63 off away from the static hub 46. Accordingly, in these versions of the invention, a flat ring formed of a low friction plastic such as the plastic sold under the trademark TEFLON by the du Pont Company, may be fitted around the forward end of the rotating tube main body 66. This ring serves as a bearing to minimize the friction between the rotating hub 63 and the static hub 46.

Alternatively, in some versions of the invention, the distal end of the inlet fitting 108 may seat in a counter bore formed integral with fluid inlet bore 54. An advantage of this version of the invention is that it may eliminate the need to provide the irrigation seal 56 around bore 54.

Also, alternative versions of the motor may be provided. For example, while not optimal, the stator may be embedded in the rotating hub 63 and the magnets may be mounted to the handpiece. In these versions of the invention, some type of brushes integral with the handpiece would provide an electrical path between the control console 28 and the windings integral with the stator. Also, in some versions of the invention Hall sensors may be mounted in the handpiece 20. These sensors would provide signals that indicate the rotational position of the rotating hub magnets 124. The control console 28, in turn, uses the signals representative of the position of these magnets as an input for regulating the energization of the stator windings.

Moreover, it should likewise be understood that the rotating hub 63 may be provided with more or less magnets 124 than has been described. Typically, the rotating hub 63 will be provided with an even number of magnets. Similarly, stator 122 may have other constructions than what has been described.

Figure 16:
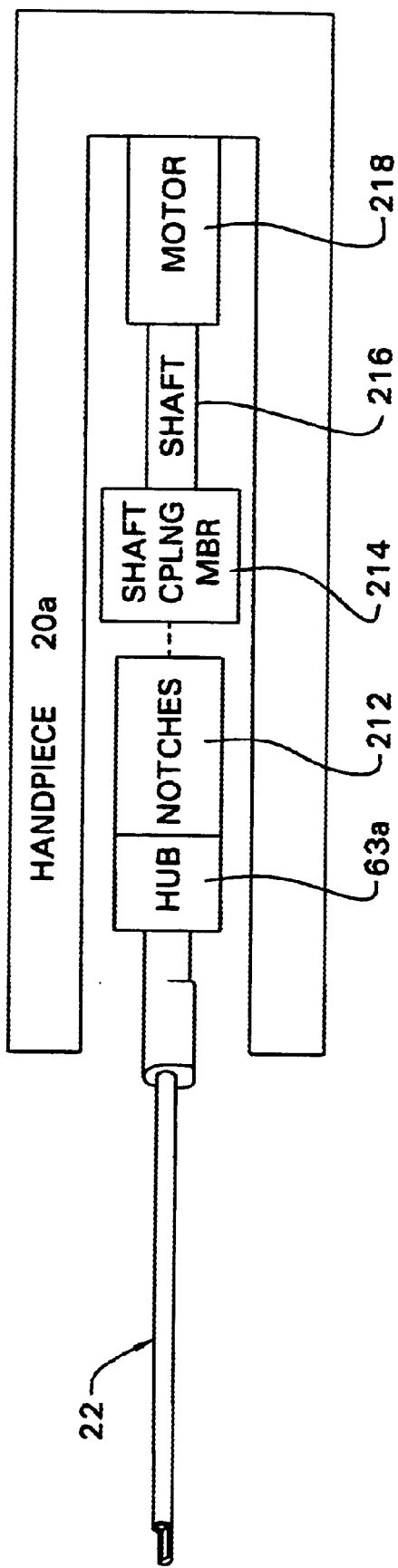
FIG. 16 is a block diagram of how an alternative cutting accessory is coupled to an alternative shaft of an alternative handpiece of this invention.

It should likewise be appreciated that there may be versions of the invention in which no part of the motor is built into the cutting accessory 22. In these versions of the invention, as seen in FIG. 16, the rotating hub 63a may be provided with notches 212 or other means for engaging a complementary coupling member 214 that is integral with the shaft 216 of the motor 218 built into the handpiece 20a. In these versions of the invention, once the rotating hub engages with the shaft, the hub, as well as inner tube 79 rotate in unison with the shaft.

Also, it should be clear that the structure of the valve member may very from what has been described. Clearly, the valve member can rotate along an axis different than the longitudinal axis that runs through the handpiece 20. It should be clear that, in these versions of the invention the conduits in the end cap 156 will have different orientations than what has been described. Furthermore, there is no requirement that in all versions of the invention in which the handpiece 20 is capable of directing a purge flow through the suction conduit of the cutting accessory 22 that the handpiece also have a switch assembly for controlling the rate of the purge flow. Similarly, in other versions of the invention, by appropriately designing the components, it may be possible to provide one of two purge flows to the suction conduit; a first low-pressure flow and a second high-pressure flow. This arrangement may be possible by constructing the handpiece so that only after irrigation bore opening 178 is placed in full registration with the valve member opening 182 does the reed switch, upon further actuation of the slide lever 40, close.

Moreover, in other versions of the invention, a switch assembly for regulating the energization of the suction pump 38 may be built into the handpiece. This switch assembly may include a second reed switch that is actuated by magnet 208 or a second magnet that is displaced by the actuation of slide lever 40. Depending on the open/closed state of this reed switch, the control console 28 may either increase or decrease the suction drawn by pump 38.

Therefore, it is an object of the appended claims to cover all such modifications as come within the true spirit and scope of this invention.

What is claimed is:

1. A powered surgical handpiece for actuating a cutting accessory, the cutting accessory having a first member that is formed with a conduit, said handpiece including:

a body, said body being formed with: opposed front and rear ends; an accessory bore in the front end for receiving the cutting accessory; a suction bore through which a suction is drawn; and an irrigation conduit through which irrigation fluid is introduced into said body;

a coupling assembly attached to said body for releasably holding the cutting accessory in the accessory bore;

a motor disposed in said body for actuating the first member of the cutting accessory; and a valve assembly including:

a valve member positioned in said body for selectively establishing a fluid communication path between the conduit of the cutting accessory first member and the suction bore or the irrigation conduit, wherein said valve member is moveable between: a first position in which said valve member establishes a fluid communication path between the conduit of the first member and the suction bore; a second position in which said valve member prevents fluid communication between the conduit of the first member and the suction bore or the irrigation conduit; and a third position in which said valve member establishes a fluid communication path between the conduit of the first member and the irrigation conduit; and a control switch located outside of said body that is movably attached to said body and that is connected to said valve member for moving said valve member between the first, second and third valve member positions.

2. The handpiece of claim 1, further including a sensor assembly disposed in said body for monitoring the position of said valve member and generating a signal representative of the valve member position.

3. The handpiece of claim 1, wherein:

said motor has a stator fixedly secured to said body; and a rotor rotatably positioned within said stator and said rotor is formed with a through bore, the through bore being directed to said valve member, the through bore providing a fluid communication path between the conduit of the cutting accessory first member and said valve member.

4. The handpiece of claim 3, wherein said rotor includes at least two magnets integrally attached to the cutting accessory first member.

5. The handpiece of claim 1, wherein, said body has a longitudinal axis and said valve member is rotatably fitted in said body to rotate around the longitudinal axis of said body.

6. The handpiece of claim 1, further including a moveable rod fitted to said body, said rod extending between said control switch and said valve member for actuating said valve member upon displacement of said control switch.

7. The handpiece of claim 6, further including a sensor mounted to said body adjacent said rod to monitor displacement of said rod, said sensor being configured to generate an output signal that varies with the displacement of said rod.

8. A surgical handpiece for actuating a cutting accessory, the cutting accessory having an outer tube and an inner tube disposed within the outer tube, the inner tube defining a conduit, said handpiece including:

a body, said body having: opposed first and second ends; an accessory bore in the first end for receiving a proximal end of the cutting accessory; and a suction bore that extends towards the second end;

a coupling assembly mounted to the first end of said body for releasably securing the outer tube to said body;

a supply tube integral with said body that extends towards the first end of said body;

a motor disposed in said body for rotating the inner tube;

a valve moveably fitted in said body, and wherein the inner tube conduit, the suction bore and said supply tube are each connected to said valve and said valve has: a first position in which said valve establishes a fluid path between the inner tube conduit and the suction bore; a second position in which said valve prevents fluid communication from between the inner tube conduit and the suction bore or said supply tube; and a third position in which said valve establishes a fluid path between the inner tube conduit and said supply tube; and a switch located outside of said body that is moveably attached to said body and connected to said valve for selectively moving said valve between the first, second and third positions.

9. The handpiece of claim 8, wherein:

said motor has a stator fixedly secured to said body; and a rotor rotatably positioned within said stator and said rotor is formed with a through bore, the through bore being directed to said valve, the through bore providing a fluid communication path between the inner tube conduit and said valve.

10. The handpiece of claim 9, wherein said rotor includes at least two magnets mounted to a hub and said hub is integrally attached to a proximal end of the inner tube.

11. The handpiece of claim 8, wherein said coupling assembly has an inlet fitting positioned to engage the cutting accessory and said supply tube has a branch line that extends to said inlet fitting.

12. The handpiece of claim 8, wherein, said body has a longitudinal axis and said valve is rotatably fitted in said body to rotate around the longitudinal axis of said body.

13. The handpiece of claim 8, further including a sensor assembly disposed in said body for monitoring the position of said valve and said sensor assembly generates an output signal representative of the position of said valve.

14. The handpiece of claim 13, wherein:

a moveable linkage member extends between said switch and said valve for displacing said valve upon displacement of said switch; and said sensor assembly includes a sensed member connected to said linkage member to move with the movement of said linkage member and a sensing device mounted to said body that generates the sensor output signal as a function of the relative distance of said sensed member to said sensing device.

15. The handpiece of claim 8, wherein:

said body is formed with a valve chamber and the inner tube conduit, the suction bore and the supply tube are each connected to the valve chamber; and said valve is rotatably fitted in the valve chamber to rotate between the first, second and third valve positions.

16. A powered surgical handpiece for actuating a cutting accessory, the cutting accessory having a hub and a cutting device, said handpiece including:

a body, said body having a bore that is open at one end of said body for receiving the cutting accessory hub;

a power generating unit mounted in said body that is connected to the cutting device for actuating the cutting device;

an irrigation tube attached to said body; and a coupling arm moveably mounted to said body, said coupling arm having: at least one locking member positioned to selectively engage and disengage the cutting accessory hub for releasably holding the hub to said body; and an inlet fitting to which said irrigation tube is connected, said inlet fitting being positioned to move with said at least one locking member so that when said locking member engages the hub, said inlet fitting is in fluid communication with an inlet bore formed in the hub.

17. The handpiece of claim 16, wherein said coupling assembly includes a single locking member.

18. The handpiece of claim 16, wherein said body is formed so that the bore in which the cutting accessory hub is received has a non-circular profile.

19. The handpiece of claim 16, wherein said power generating unit is a motor.

20. The handpiece of claim 19, wherein:

the hub of the cutting accessory is an outer hub and the cutting accessory has an inner hub that is capable of rotation relative to the outer hub, the inner hub being the end of the cutting accessory cutting device that is received in the handpiece body bore;

said motor includes at least two magnets that function as a motor rotor and said magnets are mounted to the inner hub of the cutting accessory; and said locking member is positioned to engage the cutting accessory outer hub.

21. The handpiece of claim 19, wherein said motor is provided with a rotor and said rotor has a bore that provides a fluid communication path from the cutting accessory.

22. A powered surgical handpiece for actuating a cutting accessory, the cutting accessory having an outer hub and an inner hub located adjacent the outer hub, said handpiece including:

a body, said body having a front end that has a bore for receiving the inner hub of the cutting accessory;

a motor disposed in said body for rotating the inner hub of the cutting accessory;

a coupling assembly mounted to the front end of said body, said coupling assembly having a locking arm that is movable relative to said body, said locking arm having at least one locking member wherein said locking arm has a locked position in which said at least one locking member is positioned to engage the outer hub of the cutting accessory to releasably secure the outer hub to said body and a release position in which said at least one locking member is spaced from the outer hub;

a supply tube integral with said body; and an inlet fitting that is attached to said locking arm so as to move with said locking arm, said inlet fitting having an outlet opening and wherein, said supply tube is attached to said inlet fitting and, when said locking arm is in the locked position, said inlet fitting is positioned to abut an inlet port in the outer hub.

23. The handpiece of claim 22, wherein said motor includes a stator that is fixedly secured to said body and a rotor that is located within said stator and said rotor defines a bore that provides a fluid communication path to the inner hub of the cutting accessory.

24. The handpiece of claim 22, wherein said motor includes at least two magnets that are integrally attached to the inner hub of the cutting accessory and a stator disposed in said body.

25. A powered surgical handpiece for actuating a cutting accessory, the cutting accessory having an outer hub and an inner hub located adjacent the outer hub, said surgical handpiece including:

a body, said body having a proximal end and a distal end opposite the proximal end;

a power generating unit disposed in said body;

a first coupling member located adjacent the distal end of said body for releasably'securing the outer hub of the cutting accessory to said body;

a second coupling member located adjacent the distal end of said body for releasably securing the inner hub to said power generating unit so that said power generating unit and the inner hub move in unison;

a first conduit disposed in said body that extends toward the distal end of said body;

a fluid inlet fitted to said body and located adjacent the distal end of said body, wherein said first conduit is connected to said fluid inlet and said fluid inlet has an opening positioned to be in fluid communication with a complementary port formed in the inner hub; and a second conduit disposed in said body that is separate from the first conduit, said second conduit being configured to extend towards the distal end of said body; and a fluid outlet formed in said body and located adjacent the distal end of said body wherein: said second conduit is connected to said fluid outlet; and said fluid outlet is positioned so that, when said first coupling member secures the outer hub to said body, said fluid outlet is positioned to be in registration with a fluid conduit formed in the outer hub.

26. The powered surgical handpiece of claim 24, wherein:

said power generating unit is a motor that includes a rotating shaft; and said second coupling member is fitted to said shaft to releasably couple the inner hub to said shaft so that said shaft and the inner hub rotate in unison.

27. The powered surgical handpiece of claim 26, wherein: said shaft of said motor at least partially forms said first conduit and said shaft has an open end adjacent the distal end of said body, the open end of said shaft forming said fluid inlet.

28. The powered surgical handpiece of claim 25, wherein said first coupling member is movably fitted to said body, and said first coupling member has a first position in which said first coupling member is positioned to engage against a surface of the outer hub and a second position in which said first coupling member is spaced from the surface of the outer hub.

29. The powered surgical handpiece of claim 28, wherein said fluid outlet is formed in said coupling member and moves with said first coupling member.

30. The powered surgical handpiece of claim 25, wherein:

a suction fitting is mounted to said body adjacent the proximal end of said body; and said first conduit is in fluid communication with the suction fitting.

31. The powered surgical handpiece of claim 25, wherein:

an inlet fitting is mounted to said body adjacent the proximal end of said body; and said second conduit is in fluid communication with said inlet fitting.

32. The powered surgical handpiece of claim 25 wherein:

the outer hub is formed so that the fluid conduit is a bore that extends inwardly from an outer surface of said outer hub; and said fluid outlet is positioned in said body to be in registration with an end of the outer hub bore that extends from a surface of the outer hub.

33. A powered surgical handpiece for actuating a cutting accessory, the cutting accessory having an outer hub and an inner hub located adjacent the outer hub, said surgical handpiece including:

a body, said body having a proximal end and a distal end opposite the proximal end, the distal end of said body being formed to define a bore for receiving the cutting accessory hubs;

a motor disposed inside said body, said motor having a rotating shaft, said shaft having a portion that extends into the cavity formed in the distal end of said body;

a first coupling assembly fitted to said shaft to releasably couple the inner hub to said shaft so that said shaft and the inner hub will rotate in unison;

a port located in the cavity of the distal end of said body for receiving fluid discharged from the inner hub;

a first conduit disposed inside said body that extends from said port towards the proximal end of said body;

a second coupling assembly mounted to the distal end of said body for releasably holding the outer hub to said body;

a second conduit disposed inside said body that extends towards the distal end of said body; and a discharge opening formed in the distal end of said body wherein said second conduit is in fluid communication with said discharge opening and said discharge opening is positioned to be in registration with a complementary fluid conduit formed on the outer hub.

34. The powered surgical handpiece of claim 33, wherein:

a portion of said shaft at least partially forms said first conduit; and the portion of said shaft that extends into the cavity has an open end that forms said port located in the cavity.

35. The powered surgical handpiece of claim 33, wherein said second coupling assembly includes a coupling arm that is moveably attached to the distal end of said body and a coupling member is mounted to the coupling arm, wherein said coupling member is positioned to releasably engage the outer hub of the cutting accessory.

36. The powered surgical handpiece of claim 35, wherein said discharge opening is formed in said coupling arm.

37. The powered surgical handpiece of claim 36, wherein:

said shaft of said motor and said first conduit are at least partially axially aligned.

38. The powered surgical handpiece of claim 33 wherein:

the outer hub is formed so that the fluid conduit is a bore that extends inwardly from an outer surface of said outer hub; and said discharge opening is positioned in said body to be in registration with an opening in the outer hub from which the outer hub bore extends.

39. A powered surgical handpiece for actuating a cutting accessory, the cutting accessory having a drive tube that is formed with a conduit, said handpiece including:

a body, said body being formed with: a front end; an accessory bore in the front end for receiving the cutting accessory; a suction conduit through which a suction is drawn; and an irrigation conduit through which irrigation fluid is introduced into said body;

a coupling assembly attached to said body far releasably holding the cutting accessory in the accessory bore;

a motor disposed in said body for actuating the cutting accessory drive tube;

a valve assembly, said valve assembly including: a valve chamber defined by said body, wherein said suction conduit and said irrigation conduit each extend to the valve chamber and said body is further formed so that the drive tube conduit is in fluid connection with the valve chamber; a valve member moveably fitted in the valve chamber, said valve member shaped to have a flow through opening and shaped so that, upon positioning of said valve member, the flow through opening selectively establishes a fluid communication path between the drive tube conduit and the suction conduit or between the drive tube conduit and the irrigation conduit; and a switch connected to said valve member for selectively positioning said valve member.

40. The powered surgical handpiece of claim 39, wherein said body and said valve member are further shaped so that said valve member has a position in which said valve member prevents fluid communication between the drive tube conduit and the suction conduit or the irrigation conduit.

41. The powered surgical handpiece of claim 39, wherein: said motor has a stator fixedly secured to said body; and a rotor rotatably positioned within said stator and said rotor is formed with a through bore, the through bore being directed to the valve chanter, the through bore providing a fluid communication path between the drive tube conduit and the valve chamber.

42. The powered surgical handpiece of claim 41, wherein said rotor includes at least two magnets integrally attached to the cutting accessory drive tube.

43. The handpiece of claim 39, wherein, said body has a longitudinal axis and said valve member is rotatably fitted in said body to rotate around the longitudinal axis of said body.

44. The powered surgical handpiece of claim 39, further including a moveable rod fitted to said body, said rod extending between said switch and said valve member for actuating said valve member upon displacement of said switch.

45. The powered surgical handpiece at claims 39, wherein said valve member is rotatably positionable in the valve chanter.

46. A powered surgical handpiece for actuating a cutting accessory, the cutting accessory having a drive tube that defines a conduit, said handpiece comprising:

a body, said body having: an accessory bore in one end for receiving an end of the cutting accessory; a valve chamber; a fluid communications path from the drive tube conduit to the valve chamber; a suction conduit that extends from the valve chamber; an irrigation conduit that extends from the valve chamber;

a coupling assembly with at least one first coupling member moveably attached to said body that releasably engages the cutting accessory to releasably hold the cutting accessory to said body;

a motor disposed in said body, said motor including a coupling unit for engaging the drive tube to transfer rotational power developed by said motor to the drive tube;

a valve member rotatably fitted in the valve chamber of said body, said valve mentor being formed with a through opening wherein said body and said valve member are collectively shaped so that said valve member can be positioned so that the through opening establishes a fluid communication path between the drive tube conduit and the suction conduit or between the drive tube conduit and the irrigation conduit;

a switch connected to said valve member for rotating said valve member;

a suction fitting attached to said body wherein the suction conduit extends to and is fluid communication with said suction fitting; and an irrigation fitting attached to said body wherein the irrigation conduit extends to and is fluid communication with said irrigation fitting.

47. The powered surgical handpiece of claim wherein said body and said valve member are further shaped so that said valve member has a position in which said valve member prevents fluid communication between the drive tube conduit and the suction conduit or the irrigation conduit.

48. The powered surgical handpiece of claim 46, wherein: said motor has a stator fixedly secured to said body; and a rotor rotatably positioned within said stator and said rotor is formed with a through bore, the through bore being directed to the valve cavity, the through bore being at least part of the fluid communication path between the drive tube conduit and the valve chamber.

49. The powered surgical handpiece of claim 48, wherein said rotor includes at least two magnets integrally attached to the cutting accessory drive tube.

50. The handpiece of claim 46, wherein, said body has a longitudinal axis and said valve member is rotatably fitted in said body to rotate around the longitudinal axis of said body.

51. The powered surgical handpiece of claim 46, further including a moveable rod fitted to said body, said rod extending between said switch and said valve member for rotating said valve member upon displacement of said switch.

52. A powered surgical handpiece for actuating a cutting accessory, the cutting accessory having an outer hub, an elongated outer tube that extends from the outer hub and an inner tube that is disposed in the outer tube, the inner tube having a conduit, said handpiece comprising:

a body, said body having a bore for receiving the outer hub and an end of the inner tube that extends from said outer hub;

a coupling assembly attached to said body for releasably holding the outer hub to said body;

a motor, said motor including a coupling unit that engages the cutting accessory inner tube to transfer rotational power developed by said motor to the inner tube;

an inlet fitting attached to said body, said inlet fitting adapted to receive irrigation fluid;

an irrigation fluid conduit that extends from said inlet fitting to the bore in which the outer hub is received, said irrigation fluid conduit having a discharge bore that is open towards the outer hub;

a branch conduit formed in said body that extends from said irrigation fluid conduit, said branch conduit extending toward and in fluid communication with the inner tube conduit; and a valve member moveably disposed in a valve chamber formed in said body, the valve chamber being in fluid communication with the inner tube conduit and the branch conduit, said valve having a flow through opening and being positionable in said valve chamber to regulate fluid flow between the branch conduit and the inner tube conduit.

53. The powered surgical handpiece of claim 52, wherein: said motor has a stator fixedly secured to said body; and a rotor rotatably positioned within said stator and said rotor is formed with a through bore, the through bore being directed to the valve chamber, the through bore being at least part of a fluid communication path between the inner tube conduit and the valve chamber.

54. The powered surgical handpiece of claim 53, wherein said rotor includes at least two magnets integrally attached to the cutting accessory drive tube.

55. The powered surgical handpiece of claim 52, wherein:

said coupling assembly includes an arm that is moveably attached to said body for releasably engaging the cutting accessory outer hub; and said irrigation fluid conduit extends to said coupling assembly arm and the irrigation fluid outlet discharge bore is formed in said coupling assembly arm.

56. The powered surgical handpiece of claim wherein:

said body is further formed with a suction conduit that extends from the valve chamber; and said body and said valve member are collectively shaped so that said valve member selectively establishes a fluid communication path between the inner tube conduit and the branch conduit or between the inner tube conduit and the suction conduit.

* * * * *

UNITED STATES PATENT AND TRADEMARK OFFICE
CERTIFICATE OF CORRECTION

PATENT NO. : 6,689,146 B1
DATED : February 10, 2004
INVENTOR(S) : David M. Himes It is certified that error appears in the above-identified patent and that said Letters Patent is hereby corrected as shown below:

Column 15,
Line 7, change "a supply tube" to -- a supply conduit --
Lines 11-12, change "said supply tube" to -- said supply conduit --
Lines 17 and 20, change "said supply tube" to -- said supply conduit --
Line 59, change "the supply tube" to -- the supply conduit --
Line 67, change "accessory hub;" to -- accessory hub and an end of the cutting accessory cutting device; --

Column 16,
Lines 16-17, change "coupling assembly" to -- coupling arm --
Line 56, change "a supply tube" to -- a supply conduit --
Line 59, change "said supply tube is attached" to -- said supply conduit is connected --

Column 17,
Line 9, change "end and a distal end opposite the proximal end;" to -- end, a distal end opposite the proximal end and a bore in the distal end for receiving the hubs of the cutting accessory; --
Line 31, change "body and located adjacent the distal end" to -- body that opens into the bore in the distal end --
Line 38, change "of Claim 24" to -- of Claim 25 --
Line 57, change "of Claim 28" to -- of Claim 25 --
Line 58, change "said coupling member" to -- said first coupling member --

Column 18,
Line 17, change "the cavity formed" to -- the bore formed --
Line 21, change "the cavity of" to -- the bore of --
Lines 31-32, change "said body wherein" to -- said body that is open to the bore formed in the distal end of the body wherein --
Lines 36 and 37, change "said shaft" to -- said motor shaft --
Line 38, change "into the cavity has" to -- into the body distal end bore has --
Line 39, change "the cavity" to -- the body distal end bore --
Line 66, change "body far releasably" to -- body for releasably --

Column 19,
Line 27, change "the valve chanter" to -- the valve chamber --
Line 41, change "at Claims 39" to -- of Claims 39 --
Line 42, change "valve chanter" to -- valve chamber --
Line 63, change "said valve mentor" to -- said valve member --
Line 64, change "opening wherein said" to -- opening, wherein said --

UNITED STATES PATENT AND TRADEMARK OFFICE
CERTIFICATE OF CORRECTION

PATENT NO. : 6,689,146 B1
DATED : February 10, 2004
INVENTOR(S) : David M. Himes It is certified that error appears in the above-identified patent and that said Letters Patent is hereby corrected as shown below:

Column 20,
Line 11, change "of claim wherein" to -- of Claim 46, wherein --
Line 62, change "said valve having" to -- said valve member having --

Column 22,
Line 4, change "of claim wherein" to -- of Claim 52, wherein --

Signed and Sealed this

Twenty-ninth Day of June, 2004

JON W. DUDAS
*Acting Director of the United States Patent and Trademark Office*